US010034818B2

(12) United States Patent
Cropper et al.

(10) Patent No.: US 10,034,818 B2
(45) Date of Patent: Jul. 31, 2018

(54) USE OF A BENEFIT DELIVERY PARTICLE FOR MALODOUR BENEFIT

(71) Applicant: Conopco, Inc., Englewood Cliffs, NJ (US)

(72) Inventors: Martin Peter Cropper, Birkenhead (GB); Craig Warren Jones, Wirral (GB); Adam John Limer, Northwich (GB); James Merrington, Wirral (GB); Katherine Mary Thompson, Wirral (GB); Jeremy Nicholas Winter, Chester (GB)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

(21) Appl. No.: 15/313,067

(22) PCT Filed: May 20, 2015

(86) PCT No.: PCT/EP2015/061174
§ 371 (c)(1),
(2) Date: Nov. 21, 2016

(87) PCT Pub. No.: WO2015/181029
PCT Pub. Date: Dec. 3, 2015

(65) Prior Publication Data
US 2017/0181935 A1   Jun. 29, 2017

(30) Foreign Application Priority Data

May 28, 2014  (EP) .................................. 14170236
May 28, 2014  (EP) .................................. 14170237

(51) Int. Cl.
| | | |
|---|---|---|
| *A61K 8/87* | (2006.01) | |
| *A61K 8/02* | (2006.01) | |
| *A61K 8/84* | (2006.01) | |
| *A61Q 15/00* | (2006.01) | |
| *A61K 8/81* | (2006.01) | |

(52) U.S. Cl.
CPC .......... *A61K 8/0241* (2013.01); *A61K 8/8152* (2013.01); *A61K 8/84* (2013.01); *A61K 8/87* (2013.01); *A61Q 15/00* (2013.01); *A61K 2800/412* (2013.01); *A61K 2800/624* (2013.01); *A61K 2800/654* (2013.01)

(58) Field of Classification Search
CPC .......... A61Q 15/00; A61Q 13/00; A61K 8/87; A61K 8/84; A61K 8/81
See application file for complete search history.

(56) References Cited

U.S. PATENT DOCUMENTS

| | | |
|---|---|---|
| 7,341,674 B1 | 3/2008 | Trinh et al. |
| 9,321,987 B2 | 4/2016 | Jones et al. |
| 9,414,997 B2 | 8/2016 | Jones et al. |
| 2004/0072719 A1 | 4/2004 | Bennett et al. |
| 2009/0048365 A1 | 2/2009 | Brain |
| 2011/0021409 A1 | 1/2011 | Cox et al. |
| 2011/0059179 A1 | 3/2011 | Shefer |

FOREIGN PATENT DOCUMENTS

| | | | |
|---|---|---|---|
| EP | 0761201 | | 1/2002 |
| EP | 1533365 | | 5/2005 |
| EP | 1541121 | | 6/2005 |
| EP | 1627664 | | 2/2006 |
| WO | WO9842818 | | 10/1998 |
| WO | WO2003089561 | | 10/2003 |
| WO | WO2004067584 | | 8/2004 |
| WO | WO2005025626 | | 3/2005 |
| WO | WO2007141742 | | 12/2007 |
| WO | WO2008058868 | | 5/2008 |
| WO | WO2009037482 | | 3/2009 |
| WO | 2009101000 | * | 8/2009 |
| WO | WO2009101000 | | 8/2009 |
| WO | WO2010056321 | | 5/2010 |
| WO | WO2011158962 | | 12/2011 |
| WO | WO2012007438 | | 1/2012 |
| WO | WO2013026657 | | 2/2013 |
| WO | WO2013107581 | | 7/2013 |
| WO | WO2014075956 | | 5/2014 |
| WO | WO2014079745 | | 5/2014 |
| WO | WO2015181027 | | 12/2015 |

OTHER PUBLICATIONS

Search Report & Written Opinion in CTEP2015061174, dated Aug. 4, 2015.
Search Report & Written Opinion in EP14170236, dated Dec. 3, 2014.
Search Report & Written Opinion in EP14170237, dated Dec. 16, 2014.
Search Report & Written Opinion in PCTEP2015061161, dated Nov. 1, 2015.
Simon D et al., the effect of the dry glass transition on the synthesis of paraffin microcapsules obtained by suspension-like polymerization, Polymer Engineering & Science, Jan. 1, 2014, pp. 208-214, XP002732641, v. 54, No. 1, ES.
Co-Pending Application; Applicant; Cropper et al., filed; Nov. 21, 2016.
Co-Pending U.S. Appl. No. 15/313,072; Applicant: Martin Peter Cropper, filed: Nov. 21, 2016.

* cited by examiner

*Primary Examiner* — Carlos A Azpuru

(74) *Attorney, Agent, or Firm* — Karen E. Klumas

(57) ABSTRACT

The invention provides a use of a particle to absorb and retain odiferous compounds, wherein the particle comprises: —(a) a solid core comprising a first hydrophobic polymer, and (b) a shell comprising a second hydrophobic polymer wherein the Tg of the first hydrophobic polymer is lower than the Tg of the second hydrophobic polymer; wherein the particles have a mean particle size of less than 1 micron, preferably from 0.1 to 0.3 microns, and wherein the odiferous compound is a malodor compound.

17 Claims, No Drawings

USE OF A BENEFIT DELIVERY PARTICLE FOR MALODOUR BENEFIT

TECHNICAL FIELD

The present invention is concerned with the use of particles for the absorption of malodour. The use of the particles has a broad application in personal care and home care applications and will be specifically disclosed herein in the context of skin (deo) and hair uses, but also applies to household care and laundry.

BACKGROUND

Many home and personal care formulations seek to deliver so-called benefit agents to substrates such as cloth, hair and skin. Encapsulation of the benefit agent in particles has been proposed as a means of enhancing delivery, which is advantageous because of the expense of some benefit agents. Delivery of particles per se can also be useful where the particles, even in the absence of specific benefit agents, confer a benefit.

Improved delivery of fragrance is one such benefit that has been highly explored over recent years. However, perceptions of "freshness" depend not only on the positive hedonics provided by fragrance but also on effective control of malodours. For example, malodour control is important on the skin, for example in the underarm, on feet, and on the scalp, as well as on hair, on laundered textiles and on hard surfaces, such as the toilet bowl or drains.

The use of polymeric particles to absorb odours and malodours in formulations is known. For example, US 2011/0021409 and WO 2009/101000 (Henkel) disclose detergents containing porous polyamide particles and their use in deodorant and antiperspirant compositions. The particles are used to absorb fragrances, and unpleasant odours. US 2009/0048365 (IFF) describes an odour absorbing capsule comprising an active ingredient and an encapsulating polymer.

However, we have found that the subsequent retention of the malodour compounds is an area where improvement is required. Often, known particles readily re-release the malodour compounds, along with fragrance compounds.

EP 1 533 365A (IFF) discloses a process for imparting a fragrance to and/or eliminating a malodour from a surface using particles comprising a polymer (preferably ethylene-vinyl acetate copolymer, ethylcellulose, polystyrene or PMMA) having a free volume (which is effected by holes present in the polymer).

US 2011/059179 (Shefer et al) discloses a controlled delivery system for malodour management, which works by absorbing and neutralizing the malodour and releasing an odorous substance to counteract the malodour. The particles have a hydrophobic core and a film forming hydrophilic surface coating polymer.

EP 1 541 121A (Rohm & Haas) describes a system for releasing active ingredients from a composition comprising oil absorbing polymers and a coating comprising water sensitive, surface active polymers. The oil absorbing polymers have an average particle diameter of 20-1000 nm.

Many of these known particles suffer from agglomeration over time, when incorporated into home care and personal care formulations.

We have now found that particles having hydrophobic shell as well as a hydrophobic core, wherein the Tg of the shell is higher than that of the core, are capable of superior malodour absorption and retention of the malodour, and can be successfully incorporated into compositions without causing agglomeration problems.

BRIEF DESCRIPTION OF THE INVENTION

Accordingly, the present invention provides a use of a particle to absorb and retain odiferous compounds, wherein the particle comprises: —
(a) a solid core comprising a first hydrophobic polymer, and
(b) a shell comprising a second hydrophobic polymer
wherein the Tg of the first hydrophobic polymer is lower than the Tg of the second hydrophobic polymer; wherein the particles have a mean particle size of less than 1 micron, preferably from 0.1 to 0.3 microns, and wherein the odiferous compound is a malodour compound.

A second aspect of the present invention provides a use of a particle, as defined by the first aspect of the invention, which is present within a composition, wherein the composition comprises an active ingredient.

The Particle

Particles for use in the present invention have an inner region, typically forming a "core" which provides a sink for the benefit agent and a "shell" which protects the benefit agent and regulates the flow of benefit agent into and out of the core. Thus, the particle can be a carrier which controls thermodynamic (rather than kinetic) partition of the benefit agent between the interior region and elsewhere. This is particularly advantageous where late-stage addition of perfume is required as the particles and the perfume may be dosed into the product separately.

Optionally, further shells may be present, such as second and third outer shells, and so on, preferably a second shell.

Optionally, the particle comprises, a surface modification, preferably a deposition aid. In particularly preferred embodiments the deposition aid is substantive to proteinaceous, cellulosic, polyester or polyamide surfaces. By use of such a deposition aid, the efficiency of delivery to a specific substrate may be enhanced.

Where present, the surface modification will be present on the outer shell, such as where an optional further shell is present.

Particles for use in the present invention may be formed from an emulsion or miniemulsion polymerisation process.

The particle for use in the invention has an average diameter of less than 1 micron, preferably an average diameter of from 0.1 to 0.3 microns, most preferably from 0.15 to 0.3 microns.

As the particles for use in the present invention can be small, especially below 500 nm, they do not require suspending agents and thereby simplify product formulation and enable the production of clear/transparent products. Miniemulsion particles can be a small as 50 nm. A further benefit of small particles is that they are less visible in clear products. Another useful benefit is that sizes below 500 nm favour deposition on fibrous substrates and can allow formulation without the need for suspending and/or structuring systems.

DETAILED DESCRIPTION OF THE INVENTION

The Second Hydrophobic Polymer

The second hydrophobic polymer has a higher glass transition temperature (Tg) than the first hydrophobic polymer thus providing a hard outer shell over a softer inner core. The glass transition temperature is preferably greater than 100° C., more preferably greater than 120° C. This provides a shell that provides mechanical stability to the particle and prevents film formation from the core lower Tg material and prevent aggregation of the core material, which is particularly likely to happen in the presence of surfactant and solvent based formulations.

The second hydrophobic polymer preferably comprises a polyurea or a polyurethane, preferably polyurethane. Preferred polyurethanes are formed from polyisocyanates with diols and cross-linked with polyamines or polyols. Where the polyisocyanate is a diisocyanate, preferred diisocyanates may be linear aliphatic, cycloaliphatic or aromatic, preferably aromatic or cycloaliphatic.

Suitable, aromatic polyiscocyanates comprise, but are not limited to, 2,4- and 2,6-toluene diisocyanate, naphthalene diisocyanate, diphenyl methane diisocyanate and triphenyl methane-p,p'p"-trityl triisocyanate, polymethylene polyphenylene isocyanate, 2,4,4'-diphenylether triisocyanate, 3,3'-dimethyl-4,4'-diphenyl diisocyanate, 3,3'-dimethoxy-4,4'diphenyl diisocyanate, and 4,4'4"-triphenylmethane triisocyanate.

Suitable aliphatic polyisocyanates comprise, but are not limited to dicyclohexylmethane 4,4'-diisocyanate, hexamethylene-1,6-diisocyanate, isophorone diisocyanate, trimethyl-hexamethylene diisocyanate, trimer of hexamethylene-1,6-diisocyanate, trimer of isophorone diisocyanate, 1,4-cyclohexane diisocyanate, urea of hexamethylene diisocyanate, trimethylene diisocyanate, propylene-1,2-diisocyanate and butylenes-1,2-diisocyanate and mixtures thereof.

The preferred isocyanate materials are: 2,4- and 2,6-toluene diisocyanate and isophorone diisocyanate, most preferably isophorone diisocyanate.

The co-monomer used in the step-growth polymerisation is typically a diol or a diamine.

Suitable diols can comprise, but are not limited to, low molecular weight polymers such as ethylene glycol, diethylene glycol, propylene glycol, 1,4-butanediol, 2,3-butane diol, neopentyl glycol, 1,6-hexanediol, dipropylene glycol, cyclohexyl-1,4-dimethanol, 1,8-octanediol; high molecular weight polyols such as polyethylene glycol, polypropylene glycols, polytetramethylene glycols (PTMG) having average molecular weight in the range of 200 to 2000, polyester diols, diols containing carboxyl groups such as dimethylol propionic acid (DMPA) and dimethylol butanoic acid (DMBA) and mixtures thereof.

The preferred diol materials are ethylene glycol, diethylene glycol, propylene glycol, 1,4-butanediol, 2,3-butane diol, neopentyl glycol, 1,6-hexanediol, and dipropylene glycol. The more hydrophobic diols (particularly 1,4-butanediol, 2,3-butane diol, neopentyl glycol and 1,6-hexanediol) are preferred as it is generally easier to get a stable emulsion with these materials and thereby a more efficient polymerisation.

Suitable diamines can comprise amines such as ethylene diamine (EDA), phenylene diamine, toluene diamine, hexamethylene diamine, diethylenetriamine, tetraethylene pentaamine, pentamethylene hexamine, 1,6-hexane diamine, Methylene tetramine, 2,4-diamino-6-methyl-1,3,5 triazine 1,2-diaminocyclohexane, 4,4'-diamino-diphenylmethane, 1,5-diaminonaphthalene, 2,4,4'-triaminodiphenylether, bis (hexa-methylenetriamine), 1,4,5,8-tetraaminoanthraquinone, isophorone diamine, diamino propane and diaminobutane, and mixtures thereof. Polymeric amines may also be used, for example Jeffamines (polyether amine) and poly (ethyleneimine).

The preferred diamine materials are ethylene diamine and 1,6-hexane diamine. Mole ratios of the co-monomers are preferably selected such that the water soluble monomer is present in up to 10 mol % excess over the oil soluble co-monomer, preferably 1 to 8 mol % excess, more preferable 2 to 5 mol % excess. It is believed that this ensures complete reaction of isocyanate monomer.

Cross-Linking Agents for the Shell

Cross-linking agents advantageously improve the properties of the shell. Many cross-linking agents suitable for use in step-growth polymerisation are known. Cross-linking agents significantly reduce the leakage of benefit agents from the particles. Cross-linking agents are preferably polyamines and polyols.

Preferred amine-functional cross-linking agents contains more than two amine functionalities such as tetraethylene pentamine, triethylene tetraamine, 2,4,4'-triaminodiphenylether, bis(hexamethylene triamine), 1,4,5,8-tetraamino anthraquinone and diethylene triamine (DETA), and mixtures thereof.

Preferred alcohol-functional cross-linking agents contain more than two alcohol functionalities such as glycerol, pentaerythritol and 1,1,1 trihydroxmethylpropane.

Particularly preferred cross-linking agents are polyphenylisocyanate and 1,1,1-trihydroxmethylpropane.

The preferred levels of cross-linking agent are 1 to 50 mol %, more preferably 2 to 35 mol % of the step-growth monomers.

The First Hydrophobic Polymer

The particles for use in the invention have a solid core comprising a first hydrophobic polymer. The first hydrophobic polymer has a lower Tg than the second hydrophobic polymer. The first hydrophobic polymer is a rubbery polymer preferably with a glass transition temperature (Tg) preferably less than 80° C., more preferably less than 70° C. The molecular weight is preferably at least 50,000 g/mol, such as 50,000 to 10,000,000 g/mol, preferably from 100,000 to 7000,000 g/mol.

The core preferably comprises a polyacrylate polymer. Preferred polyacrylate polymers are polybutyl methacrylate, polybenzyl methacrylate, polylauryl methacrylate, poly-2-hydroxyethyl methacrylate, poly-2-hydroxypropyl methacrylates and mixtures thereof.

Free-radical polymerisation (FRP) is a suitable method of chain-growth polymerisation. In FRP a mono-functional monomer is polymerised in the presence of free-radical initiator and, optionally, a chain transfer agent. Chain transfer agents can act to reduce the average molecular weight of the final polymer.

The use of a separate chain transfer agent and an initiator is preferred. However, some molecules can perform both these functions.

The free-radical initiator can be any molecule known to initiate free-radical polymerisation such as azo-containing molecules, persulfates, redox initiators, peroxides, benzyl ketones. These initiators may be activated via thermal, photolytic or chemical means. Thermal activation is preferred.

Examples of suitable initiators include but are not limited to 2,2'-azobisisobutyronitrile (AIBN), azobis(4-cyanovaleric acid), benzoyl peroxide, cumylperoxide, 1-hydroxycyclohexyl phenyl ketone, hydrogen peroxide/ascorbic acid.

So-called 'iniferters' such as benzyl-N,N-diethyldithiocarbamate can also be used.

In some cases, more than one initiator may be used.

The preferred initiators are: 2,2'-Azobis(2-methylbutyronitrile), 2,2'-Azobis(2.4-dimethyl valeronitrile), 1,1'-Azobis (cyclohexane-1-carbonitrile) and t-butyl hydro-peroxide and t-butyl hydro-peroxide/ascorbic acid as these minimise the production of unwanted bi-products.

Preferably, the residue of the initiator in a free-radical polymerisation comprises 0 to 5 wt %, preferably 0.01 to 5 wt % and especially 0.01 to 3% wt %, of the resulting copolymer based on the total weight of the monomers.

Monomers for the chain-growth polymerisation may comprise any carbon-carbon unsaturated (or cyclic) compound which can form an addition polymer, e.g. vinyl and allyl compounds. The mono-functional monomer may be hydrophilic, hydrophobic, amphiphilic, anionic, cationic, neutral or zwitterionic in nature. Thus, the mono-functional monomer may be selected from but not limited to monomers such as vinyl acids, vinyl acid esters, vinyl aryl compounds, vinyl acid anhydrides, vinyl amides, vinyl ethers, vinyl amines, vinyl aryl amines, vinyl nitriles, vinyl ketones, and derivatives of the aforementioned compounds as well as corresponding allyl variants thereof.

Other suitable mono-functional monomers for the chain-growth polymer include hydroxyl-containing monomers and monomers which can be post-reacted to form hydroxyl groups, acid-containing or acid functional monomers, zwitterionic monomers and quaternised amino monomers.

Oligomeric or oligo-functionalised monomers may also be used, especially oligomeric (meth)acrylic acid esters such as mono(alk/aryl) (meth)acrylic acid esters of oligo[alkyleneglycol] or oligo[dimethylsiloxane] or any other mono-vinyl or allyl adduct of a low molecular weight oligomer. Mixtures of more than one monomer may also be used.

Preferred vinyl acids and derivatives thereof include (meth)acrylic acid and acid halides thereof such as (meth) acryloyl chloride.

Preferred vinyl acid esters and derivatives thereof include C1-20 alkyl(meth)acrylates (linear & branched) such as methyl (meth)acrylate, stearyl (meth)acrylate and 2-ethyl hexyl (meth)acrylate, aryl(meth)acrylates such as benzyl (meth)acrylate.

Hydrophobic monomers include: vinyl aryl compounds such as styrene and vinylbenzyl chloride; (meth)acrylic acid esters such as mono-t-butylaminoethyl (meth)acrylate, C1-20 alkyl(meth)acrylates (linear & branched), aryl(meth) acrylates such as benzyl methacrylate; oligomeric (meth) acrylic acid esters such as mono(alk/aryl)oxyoligo-[dimethylsiloxane (meth)acrylate] and tri(alkyloxy)-silylalkyl (meth)acrylates such as trimethoxysilylpropyl-(meth)acrylate.

Functional monomers, i.e. monomers with reactive pendant groups which can be post or pre-modified with another moiety can also be used such as glycidyl (meth)acrylate, trimethoxysilylpropyl(meth)acrylate, (meth)acryloyl chloride, maleic anhydride, hydroxyalkyl (meth)acrylates, (meth)acrylic acid, vinylbenzyl chloride, activated esters of (meth)acrylic acid such as N-hydroxysuccinamido (meth) acrylate and acetoxystyrene.

The copolymer may contain unreacted polymerisable groups from the multifunctional monomer.

Especially preferred monomers for chain growth polymerisation are: $C_1$-$C_{20}$ linear or branched, alkyl, alkaryl or aryl acrylates and methacrylates.

Ratio of Step-Growth to Chain Growth Polymer:

The weight percentage of step growth polymer in the combined step growth and chain growth polymers comprising the particle is typically 10% to 99%, preferably 15% to 80%, more preferably 25% to 75%.

Cross-Linking Agents for Chain-Growth Polymerisation:

Cross-linking agents can be used to modify the properties of the chain-growth polymer. Suitable materials comprise a molecule containing at least two vinyl groups that may be polymerised. The molecule may be hydrophilic, hydrophobic, amphiphilic, neutral, cationic, zwitterionic or oligomeric. Examples include di- or multivinyl esters, di- or multivinyl amides, di- or multivinyl aryl compounds and di- or multivinyl alk/aryl ethers. Typically, in the case of oligomeric or multifunctional branching agents, a linking reaction is used to attach a polymerisable moiety to a di- or multifunctional oligomer or a di- or multifunctional group. The brancher may itself have more than one branching point, such as 'T'-shaped divinylic oligomers. In some cases, more than one multifunctional monomer may be used.

Macro cross-linkers or macro branchers (multifunctional monomers typically having a molecular weight of at least 1000 Daltons) are generally formed by linking a polymerisable moiety, such as a vinyl or aryl group, to a pre-formed multifunctional polymer via a suitable linking unit such as an ester, an amide or an ether. Examples of suitable polymers include di-functional poly(alkylene oxides) such as poly (ethyleneglycol) or poly(propylene glycol), silicones such as poly(dimethyl-siloxane)s, polymers formed by ring-opening polymerisation such as poly(caprolactone) or poly(caprolactam) or poly-functional polymers formed via living polymerisation such as poly(1,4-butadiene).

Preferred macro branchers include poly(ethyleneglycol) di(meth)acrylate, poly(propyleneglycol) di(meth)acrylate, (meth)acryloxypropyl-terminated poly (dimethylsiloxane), poly(caprolactone) di(meth)acrylate and poly(caprolactam) di(meth)acrylamide.

The corresponding allyl monomers to those listed above can also be used where appropriate.

Preferred multifunctional monomers include but are not limited to divinyl aryl monomers such as divinyl benzene; (meth)acrylate diesters such as glycerol di(meth)acrylate, ethylene glycol di(meth)acrylate, propyleneglycol di(meth) acrylate and 1,3-butylenedi(meth)acrylate; oligoalkylene oxide di(meth)acrylates such as tetra ethyleneglycol di(meth)acrylate, oligo(ethyleneglycol) di(meth)acrylate and oligo(propyleneglycol) di(meth)-acrylate; divinyl acrylamides such as methylene bis-acrylamide; silicone-containing divinyl esters or amides such as (meth)acryloxypropyl-terminated oligo (dimethyl-siloxane); divinyl ethers such as oligo (ethyleneglycol)-divinyl ether; and tetra- or tri-(meth)acrylate esters such as pentaerythritol tetra-(meth)acrylate, trimethylolpropane tri(meth)acrylate or glucose di- to penta (meth)acrylate. Further examples include vinyl or allyl esters, amides or ethers of pre-formed oligomers formed via ring-opening polymerisation such as oligo(caprolactam) or oligo-(caprolactone), or oligomers formed via a living polymerisation technique such as oligo(1,4-butadiene).

Especially preferred cross-linkers are divinyl benzene, ethylene glycol di(meth)acrylate and trimethylolpropane tri (meth)acrylate.

Levels of cross-linker are typically 0 to 75, preferably 0.0001 to 50, more preferably 0.0001 to 25 mol %.

The Malodour Compounds

The particles for use in the invention are effective at absorption and retention of malodour compounds. Effective malodour retention is the efficient and prolonged association or entrapment of the malodour materials by the particles regardless of changes in the external environmental conditions (for example, temperature, humidity) or physical shear.

The use of the invention is particularly effective against malodour compounds, particularly those found in home care and personal care environments, such as toilets, skin, floors and bathrooms. Preferably, the malodour compounds are those commonly found in sweat. For example, volatile fatty acids (VFAs) and electrolytes such as isovaleric acid, 3-methyl-2-hexenoic acid and 4-methyloctanoic acid. Other common classes of malodour compound include sulfur compounds for example hydrogen sulphide, methyl mercaptans, dimethyl sulphide, 3-mercapto-2-methyl-butan-1-ol and 3-mercapto-3-methylhexan-1-ol, ammonia and amines for example trimethylamine, putrescene (1,4-diaminobutane), indole, skatole (3-methyliondole), pyrazine; aldehydes, for example acrolein and butanal, alcohols for example oct-1-en-3-ol, ketones for example oct-1-en-3-one.

The Optional Benefit Agent

Various benefit agents can be incorporated into the particles for use in the invention. Preferred benefit agents provide a skin or hair related benefit. In the alternative benefit agents may be in the laundry field, for example fabric benefit agents, and benefit agents which provide a benefit to a laundry wash and/or rinse medium.

The benefit agent may be a hydrophobic material, for example, fragrance, anti-aging agents, anti-oxidants, vitamins, anti-bacterial agents, anti-inflammatory actives, skin conditioning agents, sunscreens etc.

Suitable benefit agents include perfume raw materials, silicone oils, waxes, hydrocarbons, higher fatty acids, essential oils, lipids, skin coolants, vitamins, sunscreens, antioxidants, glycerine, malodour reducing agents, odour controlling materials, softening agents, insect and moth repelling agents, colorants, chelants, bodyfying agents, wrinkle control agents, sanitization agents, germ control agents, skin care agents, glycerine, natural actives, antibacterial actives, preservatives, antiperspirant actives, chemosensates, (for example menthol), sunless-tanning agents (for example dihydroxyacetone), emollients (for example sunflower oil and petrolatum) and mixtures thereof.

Preferred benefit agents are fragrance, skin care agents, anti-aging agents, anti-oxidants, vitamins, anti-bacterial agents, anti-inflammatory actives, skin conditioning agents, anti-perspirants, sunscreens and mixtures thereof.

Skin

For skin compositions the preferred benefit agents include one or more of fragrances, skin lightening agents, skin conditioning agents, for example 12-hydroxy stearic acid, antimicrobials, oils and insect repellents.

Antimicrobials

Preferred antimicrobials include quaternary ammonium compounds, biguanides (polyhexamethylene biguanide), phenols (e.g. Triclosan™, thymol), essential oils (such as Tea Tree Oil and Thyme Oil), climbazole, octapyrox, ketoconizole, zinc pyrithione and mixtures thereof.

Sunscreens and Skin Lightening

Preferred sunscreens and/or skin lightening agents are vitamin B3 compounds. Suitable vitamin B3 compounds are selected from niacin, niacinamide, nicotinyl alcohol, or derivatives or salts thereof. Other vitamins which act as skin lightening agents can be advantageously included in the skin lightening composition to provide for additional skin lightening effects. These include vitamin B6, vitamin C, vitamin A or their precursors. Mixtures of the vitamins can also be employed in the composition for the use of the invention. An especially preferred additional vitamin is vitamin B6. Other non-limiting examples of skin lightening agents useful herein include adapalene, aloe extract, ammonium lactate, arbutin, azelaic acid, butyl hydroxy anisole, butyl hydroxy toluene, citrate esters, deoxyarbutin, 1,3 diphenyl propane derivatives, 2, 5 di-hydroxyl benzoic acid and its derivatives, 2-(4-acetoxyphenyl)-1,3-dithane, 2-(4-hydroxyphenyl)-1,3 diethane, ellagic acid, gluc-pyranosyl-1-ascorbate, gluconic acid, glycolic acid, green tea extract, 4-Hydroxy-5-methyl-3[2H]-furanone, hydroquinone, 4-hydroxyanisole and its derivatives, 4-hydroxy benzoic acid derivatives, hydroxycaprylic acid, inositol ascorbate, kojic acid, lactic acid, lemon extract, linoleic acid, magnesium ascorbyl phosphate, 5-octanoyl salicylic acid, 2,4 resorcinol derivatives, 3,5 resorcinol derivatives, salicylic acid, 3,4,5 trihydroxybenzyl derivatives, and mixtures thereof. Preferred sunscreens useful in the present invention are 2-ethylhexyl-p-methoxycinnamate, butyl methoxy dibenzoylmethane, 2-hydroxy-4-methoxybenzophenone, octyl dimethyl-p-aminobenzoic acid and mixtures thereof. Particularly preferred sunscreen is chosen from 2-ethyl hexyl-p-methoxycinnamate, 4-t-butyl-4'-methoxydibenzoyl-methane or mixtures thereof. Other conventional sunscreen agents that are suitable for use in skin lightening compositions for use in the invention include 2-hydroxy-4-methoxybenzophenone, octyldimethyl-p-aminobenzoic acid, digalloyltrioleate, 2,2-dihydroxy-4-methoxybenzophenone, ethyl-4-(bis(hydroxypropyl)) aminobenzoate, 2-ethylhexyl-2-cyano-3,3-di phenylacrylate, 2-ethylhexylsalicylate, glyceryl-p-aminobenzoate, 3,3,5-trimethylcyclohexyl-salicylate, methylanthranilate, p-dimethyl-aminobenzoic acid or aminobenzoate, 2-ethylhexyl-p-dimethyl-amino-benzoate, 2-phenylbenzimidazole-5-sulfonic acid, 2-(p-dimethylaminophenyl)-5-sulfonic benzoxazoic acid and mixtures of these compounds.

Examples of particular sunscreen payloads are UV-B filters such as 2-ethylhexyl-4-methoxycinnamate (sold under the trade name Parsol MCX by DSM), and UV-A filters such as benzophenone or 4-tert-butyl-4'-methoxydibenzoylmethane (Avobenzone, sold under the trade name Parsol 1789 by DSM).

Antioxidants, Anti-Ageing Actives and Anti-Inflammatory Actives

Suitable actives include Retinol (Vitamin A), ascorbyl palmitate (Vitamin C palmitate), Cholecalciferol (Vitamin D3), tocopheryl (Vitamin E) acetate, Vitamin E palmitate, linoleic acid (Vitamin F), carotenoids such as beta-carotene and curcumin, phenols and polyphenols (e.g. resveratrol).

Preferred anti-oxidants include vitamin E, retinol, anti-oxidants based on hydroxytoluene such as Irganox™ or commercially available antioxidants such as the Trollox™ series.

Preferred examples in the laundry field include flavours and fragrances, enzymes, antifoams, fluorescer, shading dyes and/or pigments, conditioning agents (for example water-insoluble quaternary ammonium materials and/or silicones), sunscreens, ceramides, antioxidants, reducing agents, sequestrants, colour care additives, density matching polymers, photo-bleaches, lubricants, unsaturated oils, emollients/moisturiser and antimicrobial agents.

Perfumes

Perfume (also called herein fragrance) materials (which include pro-fragrances) are a particularly preferred benefit agent.

The pro-fragrance can, for example, be a food lipid. Food lipids typically contain structural units with pronounced hydrophobicity. The majority of lipids are derived from fatty acids. In these 'acyl' lipids the fatty acids are predominantly present as esters and include mono-, di-, triacyl glycerols, phospholipids, glycolipids, diol lipids, waxes, sterol esters and tocopherols. In their natural state, plant lipids comprise antioxidants to prevent their oxidation. While these may be at least in part removed during the isolation of oils from plants some antioxidants may remain. These antioxidants can be pro-fragrances. In particular, the carotenoids and related compounds including vitamin A, retinol, retinal, retinoic acid and provitamin A are capable of being converted into fragrant species including the ionones, damascones and damscenones. Preferred pro-fragrance food lipids include olive oil, palm oil, canola oil, squalene, sunflower seed oil, wheat germ oil, almond oil, coconut oil, grape seed oil, rapeseed oil, castor oil, corn oil, cottonseed oil, safflower oil, groundnut oil, poppy seed oil, palm kernel oil, rice bran oil, sesame oil, soybean oil, pumpkin seed oil, jojoba oil and mustard seed oil. Perfume components which are odiferous materials are described in further detail below.

The perfume is typically present in an amount of from 10 to 85 wt % of the particle, preferably from 15 to 75 wt % of the particle. The perfume suitably has a molecular weight of from 50 to 500 Dalton. Pro-fragrances can be of higher molecular weight, being typically 1 to 10 kDa.

Useful components of the perfume include materials of both natural and synthetic origin. They include single compounds and mixtures. Specific examples of such components may be found in the literature, e.g., in Fenaroli's Handbook of Flavour Ingredients, 1975, CRC Press; Synthetic Food Adjuncts, 1947 by M. B. Jacobs, edited by Van Nostrand; or Perfume and Flavour Chemicals by S. Arctander 1969, Montclair, N.J. (USA). These substances are well known to the person skilled in the art of perfuming, flavouring, and/or aromatizing consumer products, i.e., of imparting an odour and/or a flavour or taste to a consumer product traditionally perfumed or flavoured, or of modifying the odour and/or taste of said consumer product.

By perfume in this context is not only meant a fully formulated product fragrance, but also selected components of that fragrance, particularly those which are prone to loss, such as the so-called 'top notes'.

Top notes are defined by Poucher (Journal of the Society of Cosmetic Chemists 6(2):80 [1955]). Examples of well-known top-notes include citrus oils, linalool, linalyl acetate, lavender, dihydromyrcenol, rose oxide and cis-3-hexanol. Top notes typically comprise 15 to 25 wt % of a perfume composition and in those embodiments of the invention which contain an increased level of top-notes it is envisaged at that least 20 wt % would be present within the particle.

Typical perfume components which it is advantageous to employ in the embodiments of the present invention include those with a relatively low boiling point, preferably those with a boiling point of less than 300, preferably 100 to 250° C.

It is also advantageous to encapsulate perfume components which have a low Log P (i.e. those which will be partitioned into water), preferably with a Log P of less than 3.0. These materials, of relatively low boiling point and relatively low Log P have been called the "delayed blooming" perfume ingredients and include the following materials:

Allyl Caproate, Amyl Acetate, Amyl Propionate, Anisic Aldehyde, Anisole, Benzaldehyde, Benzyl Acetate, Benzyl Acetone, Benzyl Alcohol, Benzyl Formate, Benzyl Iso Valerate, Benzyl Propionate, Beta Gamma Hexenol, Camphor Gum, Laevo-Carvone, d-Carvone, Cinnamic Alcohol, Cinamyl Formate, Cis-Jasmone, cis-3-Hexenyl Acetate, Cuminic Alcohol, Cyclal C, Dimethyl Benzyl Carbinol, Dimethyl Benzyl Carbinol Acetate, Ethyl Acetate, Ethyl Aceto Acetate, Ethyl Amyl Ketone, Ethyl Benzoate, Ethyl Butyrate, Ethyl Hexyl Ketone, Ethyl Phenyl Acetate, Eucalyptol, Eugenol, Fenchyl Acetate, Flor Acetate (tricyclo Decenyl Acetate), Frutene (tricycico Decenyl Propionate), Geraniol, Hexenol, Hexenyl Acetate, Hexyl Acetate, Hexyl Formate, Hydratropic Alcohol, Hydroxycitronellal, Indone, Isoamyl Alcohol, Iso Menthone, Isopulegyl Acetate, Isoquinolone, Ligustral, Linalool, Linalool Oxide, Linalyl Formate, Menthone, Menthyl Acetphenone, Methyl Amyl Ketone, Methyl Anthranilate, Methyl Benzoate, Methyl Benyl Acetate, Methyl Eugenol, Methyl Heptenone, Methyl Heptine Carbonate, Methyl Heptyl Ketone, Methyl Hexyl Ketone, Methyl Phenyl Carbinyl Acetate, Methyl Salicylate, Methyl-N-Methyl Anthranilate, Nerol, Octalactone, Octyl Alcohol, p-Cresol, p-Cresol Methyl Ether, p-Methoxy Acetophenone, p-Methyl Acetophenone, Phenoxy Ethanol, Phenyl Acetaldehyde, Phenyl Ethyl Acetate, Phenyl Ethyl Alcohol, Phenyl Ethyl Dimethyl Carbinol, Prenyl Acetate, Propyl Bornate, Pulegone, Rose Oxide, Safrole, 4-Terpinenol, Alpha-Terpinenol, and/or Viridine.

It is commonplace for a plurality of perfume components to be present in a formulation. E.g. four or more, preferably five or more, more preferably six or more or even seven or more different perfume components from the list given of delayed blooming perfumes given above present in the particles.

The compositions may contain both encapsulated fragrance and non-encapsulated fragrance. The combined weight of encapsulated and non-encapsulated fragrance is often at least 0.5 wt % of the total composition and in many suitable compositions is up to 8 wt %, and in many desirable embodiments is from 1 to 5 wt %. The weight of non-encapsulated fragrance is commonly at least 0.1 wt % of the total composition, often at least 0.2 wt % and particularly at least 0.4 wt %. In many desirable embodiments, the compositions contain up to 2 wt % non-encapsulated fragrance based on the total composition (propellant-free). The weight ratio of the encapsulated fragrance to non-encapsulated fragrance is at the discretion of the formulator, but in practice is often at least 1:10, in many compositions at least 1:5 and in some preferred compositions at least 1:3. Said weight ratio is commonly up to 10:1, often up to 5:1 and in at least some desirable compositions is up to 3:1.

Subject to the aforementioned constraints, the respective fragrances can comprise any perfume component or preferably a mixture of components. Each fragrance commonly comprises at least 6 components, particularly at least 12 components and often at least 20 components.

The perfume component oils herein commonly have a ClogP value of at least 0.1 and often at least 0.5.

Representative fragrance oils having a boiling point of below 250° C. at 1 bar pressure include the following materials: —anethol, methyl heptine carbonate, ethyl aceto acetate, para cymene, nerol, decyl aldehyde, para cresol, methyl phenyl carbinyl acetate, ionone alpha, ionone beta, undecylenic aldehyde, undecyl aldehyde, 2,6-nonadienal, nonyl aldehyde, octyl aldehyde, phenyl acetaldehyde, anisic aldehyde, benzyl acetone, ethyl-2-methyl butyrate, damascenone, damascone alpha, damascone beta, flor acetate, frutene, fructone, herbavert, iso cyclo citral, methyl isobutenyl tetrahydro pyran, iso propyl quinoline, 2,6-nonadien-1-ol, 2-methoxy-3-(2-methylpropyl)-pyrazine, methyl octine carbonate, thdecene-2-nithle, allyl amyl glycolate, cyclogalbanate, cyclal C, melonal, gamma nonalactone, cis 1,3-oxathiane-2-methyl-4-propyl, benzaldehyde, benzyl acetate, camphor, carvone, borneol, bornyl acetate, decyl alcohol, eucalyptol, linalool, hexyl acetate, iso-amyl acetate, thymol, carvacrol, limonene, menthol, iso-amyl alcohol, phenyl ethyl alcohol, alpha pinene, alpha terpineol, citronellol, alpha thujone, benzyl alcohol, beta gamma hexenol, dimethyl benzyl carbinol, phenyl ethyl dimethyl carbinol, adoxal, allyl cyclohexane propionate, beta pinene, citral, citronellyl acetate, citronellal nitrile, dihydro myrcenol, geraniol, geranyl acetate, geranyl nitrile, hydroquinone dimethyl ether, hydroxycitronellal, linalyl acetate, phenyl acetaldehyde dimethyl acetal, phenyl propyl alcohol, prenyl acetate, triplal, tetrahydrolinalool, verdox, and cis-3-hexenyl acetate.

Representative fragrance oils having a boiling point at 1 bar pressure of at least 250° C. include: —ethyl methyl phenyl glycidate, ethyl vanillin, heliotropin, indol, methyl anthranilate, vanillin, amyl salicylate, coumarin, ambrox, bacdanol, benzyl salicylate, butyl anthranilate, cetalox, ebanol, cis-3-hexenyl salicylate, lilial, gamma undecalactone, gamma dodecalactone, gamma decalactone, calone, cymal, dihydro iso jasmonate, iso eugenol, lyral, methyl beta naphthyl ketone, beta naphthol methyl ether, para hydroxyl phenyl butanone, 8-cyclohexadecen-1-one, oxocyclohexadecen-2-one/habanolide, florhydral, intreleven aldehyde eugenol, amyl cinnamic aldehyde, hexyl cinnamic aldehyde, hexyl salicylate, methyl dihydro jasmonate, sandalore, veloutone, undecavertol, exaltolide/cyclopentadecanolide, zingerone, methyl cedrylone, sandela, dimethyl benzyl carbinyl butyrate, dimethyl benzyl carbinyl isobutyrate, triethyl citrate, cashmeran, phenoxy ethyl isobutyrate, iso eugenol acetate, helional, iso E super, ionone gamma methyl, pentalide, galaxolide, phenoxy ethyl propionate. The fragrances employed herein, either into the capsules or not encapsulated can comprise a pre-formed blend, either extracted from natural products, or possibly created synthetically. Representatives of such pre-formed blends include oils from: Bergamot, cedar atlas, cedar wood, clove, geranium, guaiac wood, jasmine, lavender, lemongrass, lily of the valley, lime, neroli, musk, orange blossom, patchouli, peach blossom, petitgrain or petotgrain, pimento, rose, rosemary, and thyme.

Aromatherapy

Another group of perfumes are the so-called 'aromatherapy' materials. These include many components also used in perfumery, including components of essential oils such as Clary Sage, *Eucalyptus*, Geranium, Lavender, Mace Extract, Neroli, Nutmeg, Spearmint, Sweet Violet Leaf and Valerian.

Insect Repellents

The benefit agent may also be an insect repellent material (where insect should be read broadly to include other pests which are arthropods but not strictly hexapods—for example ticks). Many of these materials overlap with the class of perfume components and some are odourless to humans or have a non-perfume odour. Commonly used repellents include: DEET (N,N-diethyl-m-toluamide), essential oil of the lemon eucalyptus (*Corymbia citriodora*) and its active compound p-menthane-3,8-diol (PMD), Icaridin, also known as Picaridin, D-Limonene, Bayrepel, and KBR 3023, Nepetalactone, also known as "catnip oil", Citronella oil, Permethrin, Neem oil and Bog Myrtle. Known insect repellents derived from natural sources include: *Achillea alpina*, alpha-terpinene, Basil oil (*Ocimum basilicum*), *Callicarpa americana* (Beautyberry), Camphor, Carvacrol, Castor oil (*Ricinus communis*), Catnip oil (*Nepeta* species), Cedar oil (*Cedrus atlantica*), Celery extract (*Apium graveolens*), Cinnamon (*Cinnamomum Zeylanicum*, leaf oil), Citronella oil (*Cymbopogon fleusus*), Clove oil (*Eugenia caryophyllata*), Eucalyptus oil (70%+eucalyptol, also known as cineol), Fennel oil (*Foeniculum vulgare*), Garlic Oil (*Allium sativum*), Geranium oil (also known as *Pelargonium graveolens*), Lavender oil (*Lavandula officinalis*), Lemon *eucalyptus* (*Corymbia citriodora*) essential oil and its active ingredient p-menthane-3,8-diol (PMD), Lemongrass oil (*Cymbopogon flexuosus*), Marigolds (*Tagetes* species), Marjoram (*Tetranychus urticae* and *Eutetranychus orientalis*), Neem oil (*Azadirachta indica*), Oleic acid, Peppermint (*Menthaxpiperita*), Pennyroyal (*Mentha pulegium*), Pyrethrum (from *Chrysanthemum* species, particularly *C. cinerariifolium* and *C. coccineum*), Rosemary oil (*Rosmarinus officinalis*), Spanish Flag *Lantana camara* (*Helopeltis theivora*), *Solanum villosum* berry juice, Tea tree oil (*Melaleuca alternifolia*) and Thyme (*Thymus* species) and mixtures thereof.

The solid body optionally comprises a carrier oil (also referred to herein as a diluent). It will be clear to a skilled person which oils are suitable for use with a certain benefit composition. The carrier oils are hydrophobic materials that are miscible in the benefit agent materials used in the present invention. Suitable oils are those having reasonable affinity for the benefit agent. Suitable materials include, but are not limited to triglyceride oil, mono and diglycerides, mineral oil, silicone oil, diethyl phthalate, polyalpha olefins, castor oil and isopropyl myristate. Preferably, the oil is a triglyceride oil, most preferably a capric/caprylic triglyceride oil.

Optional Surface Modifications and Deposition Aids

Surface modifications, including deposition aids modify the properties of the exterior of the particle. One particular benefit which can be obtained with these materials is to make the particle more substantive to a desired substrate. Desired substrates include cellulosics (including cotton), polyesters (including those employed in the manufacture of polyester fabrics) and protein-containing substrates (such as skin and hair). Deposition aids are preferably selected from non-hydrolysable cotton-substantive polymers, hydrolysable cotton-substantive polymers, polyester-substantive polymers and polymers that are substantive to skin and hair.

Preferred polysaccharide polymers, whether hydrolysable or not may be derived from a broad range of polysaccharides. Preferably, the polysaccharide is selected from the group consisting of: tamarind gum (preferably consisting of xyloglucan polymers), guar gum, locust bean gum (preferably consisting of galactomannan polymers), and other industrial gums and polymers, which include, but are not limited to, Tara, Fenugreek, Aloe, Chia, Flaxseed, *Psyllium* seed, quince seed, xanthan, gellan, welan, rhamsan, dextran, curdlan, pullulan, scleroglucan, schizophyllan, chitin, hydroxyalkyl cellulose, arabinan (preferably from sugar beets), de-branched arabinan (preferably from sugar beets), arabinoxylan (preferably from rye and wheat flour), galactan (preferably from lupin and potatoes), pectic galactan (preferably from potatoes), galactomannan (preferably from carob, and including both low and high viscosities), glucomannan, lichenan (preferably from icelandic moss), mannan (preferably from ivory nuts), pachyman, rhamnogalacturonan, acacia gum, agar, alginates, carrageenan, chitosan, clavan, hyaluronic acid, heparin, inulin, cellodextrins, cellulose, cellulose derivatives and mixtures thereof.

Preferred non-hydrolysable cotton-substantive deposition aids include non-hydrolysable polysaccharides. The polysaccharide preferably has a β-1,4-linked backbone.

Preferably the polysaccharide is a cellulose, a cellulose derivative, or another β-1,4-linked polysaccharide having an affinity for cellulose, such as polymannan, polyglucan, polyglucomannan, polyxyloglucan and polygalactomannan or a mixture thereof. More preferably, the polysaccharide is selected from the group consisting of polyxyloglucan and polygalactomannan. Most preferably, the deposition aid is locust bean gum, xyloglucan, guar gum or mixtures thereof.

Preferred hydrolysable cotton-substantive deposition aids include hydrolysable polysaccharides. These comprise a polysaccharide which has been modified to render it more water soluble by means of a group covalently attached to the polysaccharide by means of hydrolysable bond. Preferred groups may for example be independently selected from one or more of acetate, propanoate, trifluoroacetate, 2-(2-hydroxy-1-oxopropoxy) propanoate, lactate, glycolate, pyruvate, crotonate, isovalerate cinnamate, formate, salicylate, carbamate, methylcarbamate, benzoate, gluconate, methanesulphonate, toluene, sulphonate, groups and hemiester groups of fumaric, malonic, itaconic, oxalic, maleic, succinic, tartaric, aspartic, glutamic, and malic acids.

Preferred amongst such hydrolysable deposition aids is cellulose mono acetate.

Suitable and preferred polyester-substantive deposition aids include phthalate containing polymers, more preferably a polymer having one or more nonionic hydrophilic components comprising oxyethylene, polyoxyethylene, oxypropylene or polyoxypropylene segments, and, one or more hydrophobic components comprising terephthalate segments. Typically, oxyalkylene segments of these deposition aids will have a degree of polymerization of from 1 to about 400, although higher levels can be used, preferably from 100 to about 350, more preferably from 200 to about 300.

One type of preferred deposition aid is a copolymer having random blocks of ethylene terephthalate and polyethylene oxide terephthalate.

The deposition aid may be straight or branched. The preferred molecular weight of the polymeric deposition aid is in the range of from about 5 kDa to about 500 kDa, preferably 10 kDa to 500 kDa, more preferably 20 kDa to 300 kDa.

Preferably, the deposition-aid polymer is present at levels such that the ratio polymer:particle solids is in the range 1:500-3:1, preferably 1:200-1:3.

Preparation Methods

Polymerisation occurs in at least two phases.

In a first suitable process, a shell is first formed by step growth polymerisation. This shell encloses and contains the reagents for the chain-growth reaction which forms the core in a later phase.

Temporal separation of these phases is accomplished by control of the reagents present and the reaction conditions.

Typically, at least one of the components of the shell-forming reaction is withheld from the initial reaction mixture and added gradually to control the progress of the reaction in the first phase.

Advantageously, the first phase of the reaction is performed under conditions in which the chain-growth reaction is inhibited. These conditions include a sufficiently low temperature (for a thermally activated reaction) or conditions of sufficiently low light (for a photo-activated reaction).

Once the shell-forming reaction has proceeded sufficiently, the conditions are modified (for example, by raising the temperature or exposing the reaction mixture to light) to cause the reaction to form the inner region to start.

The preferred method is one in which an emulsion is formed comprising the chain-growth polymer components in a non-aqueous dispersed phase and the step-growth polymer components are at the interface between the dispersed phase and the continuous aqueous phase.

Typically the aqueous phase comprises an emulsifying agent, and one of the co-monomers for the step-growth polymer. It may also contain any diol, alcohol or amine cross-linking agent.

The disperse phase comprises the chain-growth monomer, the initiator, any isocyanate or vinyl cross-linking agents, the other co-monomer for the step growth polymer and any optional benefit agent.

The benefit agent may be present in the reaction mixture, at a level to give the benefit agent levels in the resulting particles at the levels disclosed above, although it is also possible to form "empty" particles and subsequently expose them to a benefit agent which can be adsorbed into the inner region.

Surface modification materials are generally added to the aqueous phase towards the end of the process, where, for example, further monomer(s) can be added to form further shell material and bind additional materials to the outside of the particle.

A second process of production of the particles involves firstly forming the core by a chain growth polymerisation process and secondly introduction of additional reagents to produce the shell by a second chain growth polymerisation process.

If used, the deposition aid polymer may be grafted to the particles by formation of an additional shell formed by a chain growth polymerisation process.

Emulsifying Agents

Many emulsifying agents are known for use in emulsion polymerisation. Suitable emulsifying agents for use in the polymerisation process may comprise, but are not limited to, non-ionic surfactants such as polyvinylpyrrolidone (PVP), polyethylene glycol sorbitan monolaurate (Tween 20), polyethylene glycol sorbitan monopalmitate (tween 40), polyethylene glycol sorbitan monooleate (Tween 80), polyvinyl alcohol (PVA), and poly(ethoxy)nonyl phenol, ethylene maleic anhydride (EMA) copolymer, Easy-Sperse™ (from ISP Technologies Inc.), ionic surfactants such as partially neutralized salts of polyacrylic acids such as sodium or potassium polyacrylate or sodium or potassium polymethacrylate. Brij™-35, Hypermer™ A 60, or sodium lignosulphate, and mixtures thereof.

Emulsifiers may also include, but are not limited to, acrylic acid-alkyl acrylate copolymer, poly(acrylic acid), polyoxyalkylene sorbitan fatty esters, polyalkylene co-carboxy anhydrides, polyalkylene co-maleic anhydrides, poly(methyl vinyl ether-co-maleic anhydride), poly(propylene-co-maleic anhydride), poly(butadiene co-maleic anhydride), and poly(vinyl acetate-co-maleic anhydride), polyvinyl alcohols, polyalkylene glycols, polyoxyalkylene glycols, and mixtures thereof.

Preferred emulsifying agents are fatty alcohol exthoylates (particularly of the Brij™ class), salts of ether sulphates (including SLES), alkyl and alkaryl sulphonates and sulphates (including LAS and SDS) and cationic quaternary salts (including CTAC and CTAB).

It is particularly preferred that the emulsifying agent comprises a nonionic surfactant. This is believed to produce a particle which deposits better on cloth than one produced solely with an anionic surfactant emulsifier, as cloth become anionic during a wash. It is also preferred that the non-ionic surfactant is hydrophilic, so as to promote the formation of a stable mini-emulsion. The alcohol ethoxylates with more than ten moles of ethoxylation, for example Synperonic A20 (C13 20EO) and Brij 58 (C16EO20), yield good results. DLS data for samples shows that as the level of surfactant increases the particle size becomes smaller, which is also advantageous. Preferably, the ratio of non-ionic to anionic emulsifier should be greater than 1:1 (i.e. non-ionic is present in excess) and the total surfactant level should be >3% wt of the polymerisation mixture.

Co-Surfactant:

Typically a co-surfactant will be present in the dispersed phase and in the resulting particle. Suitable co-surfactants for use in the present invention include hexadecane, cetyl alcohol, lauroyl peroxide, n-dodecyl mercaptan, dodecyl methacrylate, stearyl methacrylate, polystyrene, polydecene, mineral oils, isopropyl myristate $C_{13}$-$C_{15}$ alkyl benzoate and polymethyl methacrylate.

The preferred cosurfactants comprise hexadecane, polydecene and isopropyl myristate.

As a wt % of oil phase as a total, the co-surfactant is typically 0 to 20 wt %, preferably 1 to 15 wt %, more preferably 2 to 12.5 wt %.

Catalyst

Optional catalyst may be present in the dispersed phase of the emulsion. This advantageously minimises the hydrolysis of isocyanate to primary amine, which can react with further isocyanate to form polyurea during the production of polyurethane. This unwanted reaction can result in an excess of diol being left at the end of the process which can potentially lead to the formation of malodour and interfere with cross-linking reactions.

Suitable catalysts may comprise amino or organo-metallic compounds such as N,N'-dimethylaminoethanol, N,N'-dimethylcyclohexylamine, bis-(2-dimethylaminoethyl) ether, N,N'-dimethylacetylamine, diaminobicyclooctane, stannous octoate and dibutyl tin dilaurate, 1,3-bis(dimethylamino) butane, pentamethyldiethylenetriamine and mixtures thereof.

The level of catalyst is typically 0.1 to 2 wt % with respect to chain-growth monomer.

Polymerisation Conditions

As noted above, polymerisation typically occurs in at least two phases. In the earlier phase the shell is preferably formed by a reaction which, in preferred embodiments occurs at less than about 60° C., typically 15 to 55° C. In the later phase the inner region is polymerised at a preferred temperature of more than about 70° C., typically 70 to 95° C.

Both reactions are allowed to proceed for sufficiently long for polymerisation to be essentially complete, 1 to 3 hours being typical for each stage.

Deposition aid may added at the end of the later phase (preferably after cooling), when for example, further shell forming material (for example further isocyanate and co-monomer) are also added to bind the deposition aid to the outer surface of the particle by the formation of further shell material which entraps a portion of the deposition aid and leads to a "hairy" particle in which the "hair" comprises the deposition aid.

Alternatively, the deposition aid can be grafted on during an additional step chain polymerisation step.

For simple core-shell particles, the core excluding benefit agent is less than or equal to 80 wt % of mass, and the shell generally 20 wt % or greater of the mass of the particle.

Preferably the emulsion polymerisation step is a so-called "mini-emulsion" polymerisation, performed with a dispersed phase droplet size of below one micron. Sufficiently fine emulsions can be obtained by a range of methods, including sonication, and/or via high shear dynamic mixers or static mixers. Mini-emulsion products have excellent suspending properties.

Use in Products

The particles for use in the invention may be incorporated into a composition. These compositions may be in any physical form e.g. a solid such as a powder or granules, a tablet, a solid bar, a paste, soft solid, gel or liquid, especially, an aqueous-based liquid.

The composition is a home or personal care composition, preferably selected from a deodorant, antiperspirant, shampoo, hair conditioner, skin care, skin cleansing product, a laundry detergent, laundry conditioner, a hard surface cleaner, floor cleaner and a soft surface refresher. Most preferably, the composition is suitable for the treatment of skin and/or hair.

The composition comprises an active ingredient. The active ingredient is preferably for the treatment of skin or hair.

Particularly suitable active ingredients include surfactants, cleaning agents, emulsifiers, chelators, solvents, polymers, antiperspirants, moisturisers, humectants and emollients, antimicrobials (antibacterials and antifungals), abrasives, skin health actives, e.g. antioxidants, and mixtures thereof. More preferably the active ingredients are selected from a surfactant, a cleaning agent, a solvent, a polymer, an antiperspirant active and mixtures thereof, most preferably surfactants.

The composition may further comprise various additional ingredients known to a person skilled in the art. Such additional ingredients include but are not limited to: perfumes, chemosensates, pigments or dyes, optical brighteners, preservatives, sunscreens, emulsifiers, gelling agents, thickening agents, humectants (e.g. glycerine, sorbitol).

Surfactants

The active ingredient may be a surfactant, selected from anionic surfactant, non-ionic surfactant, cationic surfactant, zwitterionic surfactant, amphoteric surfactant and mixtures thereof.

Where the surface is hair or scalp, the composition may comprise an alkyl sulphate and/or ethoxylated alkyl sulfate anionic surfactant, preferably at a level of from 2 to 16 wt. %, preferably from 3 to 14 wt. %, more preferably from 4 to 10 wt. %.

Preferred alkyl sulfates are $C_{8-18}$ alky sulfates, more preferably $C_{12-18}$ alkyl sulfates, preferably in the form of a salt with a solubilising cation such as sodium, potassium, ammonium or substituted ammonium. Examples are sodium lauryl sulfate (SLS) or sodium dodecyl sulfate (SDS).

Preferred alkyl ether sulfates are those having the formula: $RO(CH_2CH_2O)_nSO_3M$; wherein R is an alkyl or alkenyl having from 8 to 18 (preferably 12 to 18) carbon atoms; n is a number having an average value of greater than at least 0.5, preferably between 1 and 3; and M is a solubilising cation such as sodium, potassium, ammonium or substituted ammonium. An example is sodium lauryl ether sulfate (SLES).

A preferred ethoxylated alkyl sulfate anionic surfactant is sodium lauryl ether sulfate (SLES) having an average degree of ethoxylation of from 0.5 to 3, preferably 1 to 3.

Compositions may comprise one or more further anionic cleansing surfactants which are cosmetically acceptable and suitable for topical application to the hair.

Examples of further suitable anionic cleansing surfactants are the alkaryl sulphonates, alkyl succinates, alkyl sulphosuccinates, alkyl ether sulphosuccinates, N-alkyl sarcosinates, alkyl phosphates, alkyl ether phosphates, and alkyl ether carboxylic acids and salts thereof, especially their sodium, magnesium, ammonium and mono-, di- and triethanolamine salts. The alkyl and acyl groups generally contain from 8 to 18, preferably from 10 to 16 carbon atoms and may be unsaturated. The alkyl ether sulphosuccinates, alkyl ether phosphates and alkyl ether carboxylic acids and salts thereof may contain from 1 to 20 ethylene oxide or propylene oxide units per molecule.

Typical anionic cleansing surfactants for use in compositions include sodium oleyl succinate, ammonium lauryl sulphosuccinate, sodium lauryl ether sulphosuccinate, sodium dodecylbenzene sulphonate, triethanolamine dodecylbenzene sulphonate, lauryl ether carboxylic acid and sodium N-lauryl sarcosinate.

Suitable preferred additional anionic cleansing surfactants are sodium lauryl ether sulphosuccinate(n)EO, (where n is from 1 to 3), lauryl ether carboxylic acid (n) EO (where n is from 10 to 20).

Mixtures of any of the foregoing anionic cleansing surfactants may also be suitable.

If added, the total amount of additional anionic cleansing surfactant in shampoo compositions may generally range from 0.5 to 45 wt %, preferably from 1.5 to 35 wt %, more preferably from 5 to 20 wt %, calculated by total weight anionic cleansing surfactant based on the total weight of the composition.

The composition can include co-surfactants, to help impart aesthetic, physical or cleansing properties to the composition.

An example of a co-surfactant is a nonionic surfactant, which can be included in an amount ranging from 0.5 to 8 wt %, preferably from 2 to 5 wt % based on the total weight of the composition.

For example, representative nonionic surfactants that can be included in compositions for use in the invention include condensation products of aliphatic ($C_8$-$C_{18}$) primary or secondary linear or branched chain alcohols or phenols with alkylene oxides, usually ethylene oxide and generally having from 6 to 30 ethylene oxide groups.

Other representative nonionic surfactants include mono- or di-alkyl alkanolamides. Examples include coco mono- or di-ethanolamide and coco mono-isopropanolamide. Further nonionic surfactants which can be included in compositions for use in the invention are the alkyl polyglycosides (APGs). Typically, the APG is one which comprises an alkyl group connected (optionally via a bridging group) to a block of one or more glycosyl groups. Preferred APGs are defined by the following formula:

$$RO\text{-}(G)_n$$

wherein R is a branched or straight chain alkyl group which may be saturated or unsaturated and G is a saccharide group.

R may represent a mean alkyl chain length of from about $C_5$ to about $C_{20}$. Preferably R represents a mean alkyl chain length of from about $C_8$ to about $C_{12}$. Most preferably the value of R lies between about 9.5 and about 10.5. G may be selected from $C_5$ or $C_6$ monosaccharide residues, and is preferably a glucoside. G may be selected from the group comprising glucose, xylose, lactose, fructose, mannose and derivatives thereof. Preferably G is glucose.

The degree of polymerisation, n, may have a value of from about 1 to about 10 or more; preferably, the value of n lies from about 1.1 to about 2; most preferably the value of n lies from about 1.3 to about 1.5.

Suitable alkyl polyglycosides for use in the invention are commercially available and include for example those materials identified as: Oramix NS10 ex Seppic; Plantaren 1200 and Plantaren 2000 ex Henkel.

Other sugar-derived nonionic surfactants which can be included in compositions for use in the invention include the $C_{10}$-$C_{18}$ N-alkyl ($C_1$-$C_6$) polyhydroxy fatty acid amides, such as the $C_{12}$-$C_{18}$ N-methyl glucamides, as described for example in WO 92/06154 and U.S. Pat. No. 5,194,639, and the N-alkoxy polyhydroxy fatty acid amides, such as $C_{10}$-$C_{18}$ N-(3-methoxypropyl) glucamide.

A preferred example of a co-surfactant is an amphoteric or zwitterionic surfactant, which can be included in an amount ranging from 0.1 to about 10 wt %, preferably from 0.5 to 8, more preferably from 1 to 5 wt %, based on the total weight of the composition.

Examples of amphoteric or zwitterionic surfactants include alkyl amine oxides, alkyl betaines, alkyl amidopropyl betaines, alkyl sulphobetaines (sultaines), alkyl glycinates, alkyl carboxyglycinates, alkyl amphoacetates, alkyl amphopropionates, alkylamphoglycinates, alkyl amidopropyl hydroxysultaines, acyl taurates and acyl glutamates, wherein the alkyl and acyl groups have from 8 to 19 carbon atoms. Typical amphoteric and zwitterionic surfactants for use in shampoos for use in the invention include lauryl amine oxide, cocodimethyl sulphopropyl betaine, lauryl betaine, cocamidopropyl betaine and sodium cocoamphoacetate.

A particularly preferred amphoteric or zwitterionic surfactant is cocamidopropyl betaine.

Mixtures of any of the foregoing amphoteric or zwitterionic surfactants may also be suitable. Preferred mixtures are those of cocamidopropyl betaine with further amphoteric or zwitterionic surfactants as described above. A preferred further amphoteric or zwitterionic surfactant is sodium cocoamphoacetate.

The total amount of surfactant (including any co-surfactant, and/or any emulsifier) in a composition is generally from 1 to 50 wt %, preferably from 2 to 40 wt %, more preferably from 10 to 25 wt % total surfactant based on the total weight of the composition.

Further Optional Ingredients

The compositions for use in the invention may contain one or more other ingredients. Such ingredients include further preservatives (e.g. bactericides), pH buffering agents, perfume carriers, polyelectrolytes, anti-wrinkle agents, anti-oxidants, sunscreens, anti-corrosion agents, pearlisers and/or opacifiers, natural oils/extracts, processing aids, eg electrolytes, hygiene agents, eg anti-bacterials and antifungals, thickeners, skin benefit agents, colourants, whiteners, gel-control agents, freeze-thaw stabilisers, bactericides, preservatives (for example 1,2-benzisothiazolin-3-one), hydrotropes, perfumes and mixtures thereof.

The compositions for use in the invention may also contain pH modifiers such as hydrochloric acid or lactic acid.

Although it is particularly suitable to employ anhydrous compositions herein, which is to say compositions that do not contain a discernible aqueous phase, any water present being associated with some other ingredient. The antiperspirant or deodorant compositions can additionally comprise an aqueous phase, and commonly together with an oil phase, the composition is in the form of an emulsion. In such compositions, the aqueous phase commonly constitutes from 10 wt % and particularly from 30 wt % of the total composition, often up to 97 wt %. The balance of the composition comprises the oil phase, including any suspended material and the emulsifier or emulsifiers. Emulsions particularly suitably comprise shear-sensitive encapsulated fragrance.

The composition preferably contains an antiperspirant active. Antiperspirant actives are preferably incorporated in an amount of from 0.5 to 50 wt %, particularly from 5 to 30 wt % and especially from 10% to 26 wt % of the composition. It is often considered that the main benefit from incorporating of up to 5 wt % of an antiperspirant active in a stick composition is manifest in reducing body odour, and that as the proportion of antiperspirant active increases, so the efficacy of that composition at controlling perspiration increases.

Antiperspirant actives for use herein are often selected from astringent active salts, including in particular aluminium, zirconium and mixed aluminium/zirconium salts, including both inorganic salts, salts with organic anions and complexes. Preferred astringent salts include aluminium, zirconium and aluminium/zirconium halides and halohydrate salts, such as chlorohydrates.

Aluminium halohydrates are usually defined by the general formula: $Al_2(OH)_xQy \cdot wH_2O$ in which Q represents chlorine, bromine or iodine, x is variable from 2 to 5 and x+y=6 while $wH_2O$ represents a variable amount of hydration. Especially effective aluminium halohydrate salts, known as activated aluminium chlorohydrates, are described in EP-A-6739 (Unilever N V et al).

Zirconium actives can usually be represented by the empirical general formula: $ZrO(OH)_{2n-nz}B_z \cdot wH_2O$ in which z is a variable in the range of from 0.9 to 2.0 so that the value 2n-nz is zero or positive, n is the valency of B, and B is selected from the group consisting of chloride, other halide, sulphamate, sulphate and mixtures thereof. Possible hydration to a variable extent is represented by $wH_2O$. Preferable is that B represents chloride and the variable z lies in the range from 1.5 to 1.87. In practice, such zirconium salts are usually not employed by themselves, but as a component of a combined aluminium and zirconium-based antiperspirant.

Antiperspirant complexes based on the above-mentioned astringent aluminium and/or zirconium salts can be employed. The complex often employs a compound with a carboxylate group, and advantageously this is an amino acid. Examples of suitable amino acids include dl-tryptophan, dl-β-phenylalanine, dl-valine, dl-methionine and β-alanine, and preferably glycine. It is highly desirable to employ complexes of a combination of aluminium halohydrates and zirconium chlorohydrates together with amino acids such as glycine, which are disclosed in U.S. Pat. No. 3,792,068 (Luedders et al).

The proportion of solid antiperspirant salt in a suspension (anhydrous) composition normally includes the weight of any water of hydration and any complexing agent that may also be present in the solid active.

For incorporation of compositions for use in the present invention, desirably at least 90 wt %, preferably at least 95 wt % and especially at least 99 wt % of the particles have a diameter in the range of from 0.1 µm up to 100 µm, and usually have an average particle diameter of at least 1 µm and especially below 20 µm. In some highly desirable contact compositions the particles by weight have a weight average particle size of at least 2 µm and particularly below 10 µm, such as in the range of from 3 to 8 µm.

Compositions for use in the invention may be emulsions. In such compositions, the antiperspirant active is commonly dissolved in the aqueous phase, commonly at a concentration in that phase of between 10 and 55 wt %. In many suitable emulsions, the concentration of antiperspirant active is chosen in relation to the weight of oils (including any non-encapsulated fragrance oils), decreasing progressively from a ratio of about 3:1 to 5:1 when the proportion of oils is below 10 wt % to a ratio in the range of 3:2 to 2:3 when the oils content is at least 50 wt % of the total composition (excluding any propellant). The compositions may include one or more thickeners or gellants (sometimes called structuring or solidifying agents) to increase the viscosity of or solidify the liquid carrier in which the particulate materials are suspended as is appropriate for application from respectively soft solid (anhydrous cream) dispensers or stick dispensers.

Compositions for use in the invention may be stick compositions. Such compositions desirably have a hardness as measured in a conventional penetration test (Seta) of less than 30 mm, preferably less than 20 mm and particularly desirably less than 15 mm. Many have a penetration of from 7 to 13 or 7.5 to 10 or 12.5 mm. The conventional penetration test employed herein, utilises a lab plant penetrometer equipped with a Seta wax needle (weight 2.5 g) which has a cone angle at the point of the needle specified to be 9° 10'+/−15'. A sample of the composition with a flat upper surface is used. The needle is lowered onto the surface of the composition and then a penetration hardness measurement is conducted by allowing the needle with its holder to drop under the combined weight of needle and holder of 50 g for a period of five seconds after which the depth of penetration is noted. Desirably the test is carried out at six points on each sample and the results are averaged. The gellants for forming stick compositions herein are usually selected from one or more of two classes: non-polymeric fibre-forming gellants and waxes, optionally supplemented by incorporation of a particulate silica and/or an oil-soluble polymeric thickener. Waxes, when employed, are often selected from hydrocarbons, linear fatty alcohols, silicone polymers, esters of fatty acids or mixtures containing such compounds along with a minority (less than 50 wt % and often less than 20 wt %) of other compounds.

Non-polymeric fibre-forming gellants, when employed, are typically dissolved in a water-immiscible blend of oils at elevated temperature and on cooling precipitate out to form a network of very thin strands that are typically no more than a few molecules wide. One particularly effective category of such thickeners comprises N-acyl aminoacid amides and in particular linear and branched N-acyl glutamic acid dialkylamides, such as in particular N-lauroyl glutamic acid di n-butylamide and N-ethylhexanoyl glutamic acid di n-butylamide and especially mixtures thereof. Such amido gellants can be employed in anhydrous compositions for use in the present invention, if desired, with 12-hydroxysteahc acid.

A gellant is often employed in a stick or soft solid composition at a concentration of from 1.5 to 30 wt %, depending on the nature of the gellant or gellants, the constitution of the oil blend and the extent of hardness desired. The anhydrous compositions can contain one or more optional ingredients, such as one or more of those selected from those identified below.

Optional ingredients include wash-off agents, often present in an amount of up to 10 wt % to assist in the removal of the formulation from skin or clothing. Such wash-off agents are typically nonionic surfactants such as esters or ethers containing a C5 to C22 alkyl moiety and a hydrophilic moiety which can comprise a polyoxyalkylene group (POE or POP) and/or a polyol.

The compositions herein can incorporate one or more cosmetic adjuncts. Such adjuncts can include skin feel improvers, such as talc or finely divided (i.e. high molecular weight) polyethylene, i.e. not a wax, for example Accumist™, in an amount of 1 up to about 10 wt %; a moisturiser, such as glycerol or polyethylene glycol (mol wt 200 to 600), for example in an amount of up to about 5 wt %; skin benefit agents such as allantoin or lipids, for example in an amount of up to 5 wt %; colours; skin cooling agents other than the already mentioned alcohols, such a menthol and menthol derivatives, often in an amount of up to 2 wt %. A further optional ingredient comprises a preservative, such as ethyl or methyl parabens or BHT (butyl hydroxy toluene) such as in an amount of from 0.01 to 0.1 wt %.

The compositions and particularly compositions intended to be delivered from a roll-on dispenser or a pump spray, conveniently comprise emulsions. In such emulsions the total oil content is often less than 10 wt %, for example comprising between 0.5 and 2 wt % of fragrance oils (non-encapsulated) and from 1 to 6 wt % of other oils, selected for example from the carrier oils described hereinbefore. It is particularly suitable to employ from 1 to 5 wt % of a triglyceride oil, such as sunflower seed oil.

Emulsions commonly employ a non-ionic surfactant acting as an emulsifier or mixture of emulsifiers providing an HLB value in the region of 6 to 10. An especially desirable range of emulsifiers comprises a hydrophilic moiety provided by a polyalkylene oxide (polyglycol), particularly polyethylene oxide, such as containing 4 to 6 EO units or a mixture of 2 to 4 plus 10 to 30 EO units and a hydrophobic moiety provided by an aliphatic hydrocarbon, preferably containing at least 10 carbons and commonly linear. The hydrophobic and hydrophilic moieties can be linked via an ester or ether linkage, possibly via an intermediate polyol such as glycerol.

Preferably the hydrophobic aliphatic substituent contains at least 12 carbons, and is derivable from lauryl, palmityl, cetyl, stearyl, olearyl and behenyl alcohol, and especially cetyl, stearyl or a mixture of cetyl and stearyl alcohols or from the corresponding carboxylic acids. Particularly conveniently, the combination of emulsifiers comprises steareth-2 and a selection from steareth-15 to steareth-30. The compositions desirably are substantially or totally free from water-soluble short chain monohydric alcohols (commonly recognised as up to $C_6$) and especially ethanol. Substantially in this context indicates a proportion of less than 5 wt % and preferably less than 1 wt % of the respective full or base composition.

Compositions for use in the invention may be aerosol compositions. Such compositions herein comprise a base composition, namely a full composition except for a propellant mixed with a propellant. The base composition commonly comprises the antiperspirant and/or deodorant active, the liquid carrier and often a suspending aid. Many suitable aerosol compositions are anhydrous. Such compositions typically have a proportion of carrier oils that is commonly from 50 to 95 wt % of the base composition, and the mixture commonly includes one or more volatile oils such as a volatile silicone oil and one or more non-volatile oils, often in a weight ratio of from 10:1 to 1:2 and particularly from 5:1 to 1:1. The concentration antiperspirant active in the base composition is often from 5% to 60 wt % and especially 10% to 45 wt %.

During the manufacture of compositions for use in the invention, it is especially desirable for the fragrance capsules to be incorporated into the composition with mixing at a rate and power input that does not damage the capsules. One convenient process sequence for preparing a stick or soft composition comprises first forming a solution of the structurant combination in the water-immiscible liquid or one of the water-immiscible liquids. This is normally carried out by agitating the mixture at a temperature sufficiently high that all the structurants dissolve (the dissolution temperature) such as a temperature in a range from 70 to 140° C. Any oil-soluble cosmetic adjunct can be introduced into oil phase, either before or after the introduction of the gellants. However, the fragrance oil, be it encapsulated or free, is commonly the last ingredient to be incorporated into the composition, after the antiperspirant active on account of its sensitivity often to elevated temperature. Commonly the resultant structurant solution is allowed to cool to a temperature that is intermediate between that at which the gellants dissolved and the temperature at which it would set, often reaching a temperature in the region of 60 to 90° C.

In some routes, the carrier oils can be mixed together prior to introduction of the gellants and the antiperspirant or deodorant active. In other preparative routes, it is desirable to dissolve all or a fraction of the gellants and especially for amido gellants in a first fraction of the composition, such as a branched aliphatic alcohol, e.g. isostearyl alcohol or octyldodecanol, optionally in conjunction with an alcohol having some water-miscibility and boiling point above the dissolution temperature of the amido gellant in the alcoholic fluid. This enables the remainder of the carrier fluids to avoid being heated to the temperature at which the structurants dissolve or melt. Such a process commonly involves mixing the fractions intensively in for example a "Sonolator"™. The fragrance capsules are most desirably introduced after any intensive mixing step. The proportion of the carrier fluids for dissolving the structurants is often from 25 to 50 wt % of the carrier fluids. In other preparative routes the particulate material is introduced into preferably a second fraction of the carrier oils, for example silicone and/or ester and/or hydrocarbon oils and thereafter, and thereafter the first fraction containing dissolved structurant and second fraction containing suspended particulate material are mixed at a temperature above that at which the composition gels, and often from 5° C. to 30° C. above the regular setting temperature of the composition, dispensing containers are filled and cooled or allowed to cool to ambient temperature.

The particles for use in the invention may be advantageously incorporated into surfactant-containing and, in particular laundry and personal care compositions. The particles are typically included in said compositions at levels of from 0.001 wt % to 10 wt %, preferably from 0.005 wt % to 7.55 wt %, most preferably from 0.01 wt % to 5 wt % of the total composition.

For laundry applications, one active ingredient in the compositions is preferably a surface active agent or a fabric conditioning agent. More than one active ingredient may be included. For some applications a mixture of active ingredients may be used.

Formulated compositions comprising the particles for use in the invention may contain a surface-active compound (surfactant) which may be chosen from soap and non-soap anionic, cationic, non-ionic, amphoteric and zwitterionic surface active compounds and mixtures thereof. Many suitable surface active compounds are available and are fully described in the literature, for example, in "Surface-Active Agents and Detergents", Volumes I and II, by Schwartz, Perry and Berch. The preferred surface-active compounds that can be used are soaps and synthetic non soap anionic, and non-ionic compounds.

The compositions for use in the invention may contain linear alkylbenzene sulphonate, particularly linear alkylbenzene sulphonates having an alkyl chain length of from C8 to C15. It is preferred if the level of linear alkylbenzene sulphonate is from 0 wt % to 30 wt %, more preferably from 1 wt % to 25 wt %, most preferably from 2 wt % to 15 wt %, of the total composition.

Compositions may contain other anionic surfactants in amounts additional to the percentages quoted above. Suitable anionic surfactants are well-known to those skilled in the art. Examples include primary and secondary alkyl sulphates, particularly C8 to C15 primary alkyl sulphates;

alkyl ether sulphates; olefin sulphonates; alkyl xylene sulphonates; dialkyl sulphosuccinates; and fatty acid ester sulphonates. Sodium salts are generally preferred.

Compositions may also contain non-ionic surfactant. Nonionic surfactants that may be used include the primary and secondary alcohol ethoxylates, especially the C8 to C20 aliphatic alcohols ethoxylated with an average of from 1 to 20 moles of ethylene oxide per mole of alcohol, and more especially the C10 to CI5 primary and secondary aliphatic alcohols ethoxylated with an average of from 1 to 10 moles of ethylene oxide per mole of alcohol. Non ethoxylated nonionic surfactants include alkylpolyglycosides, glycerol monoethers, and polyhydroxyamides (glucamide).

It is preferred if the level of non-ionic surfactant is from 0 wt % to 30 wt %, preferably from 1 wt % to 25 wt %, most preferably from 2 wt % to 15 wt %, of a fully formulated composition comprising the particles for use in the invention.

Any conventional fabric conditioning agent may be used. The conditioning agents may be cationic or non-ionic. If the fabric conditioning compound is to be employed in a main wash detergent composition the compound will typically be non-ionic. For use in the rinse phase, typically they will be cationic. They may for example be used in amounts from 0.5 wt % to 35 wt %, preferably from 1 wt % to 30 wt % more preferably from 3 wt % to 25 wt % of a fully formulated composition comprising the particles for use in the invention.

Suitable cationic fabric softening compounds are substantially water-insoluble quaternary ammonium materials comprising a single alkyl or alkenyl long chain having an average chain length greater than or equal to C20 or, more preferably, compounds comprising a polar head group and two alkyl or alkenyl chains having an average chain length greater than or equal to C14. Preferably the fabric softening compounds have two long chain alkyl or alkenyl chains each having an average chain length greater than or equal to C16. Most preferably at least 50 wt % of the long chain alkyl or alkenyl groups have a chain length of C18 or above. It is preferred if the long chain alkyl or alkenyl groups of the fabric softening compound are predominantly linear.

Quaternary ammonium compounds having two long-chain aliphatic groups, for example, distearyldimethyl ammonium chloride and di(hardened tallow alkyl) dimethyl ammonium chloride, are widely used in commercially available rinse conditioner compositions. Other examples of these cationic compounds are to be found in "Surfactants Science Series" volume 34 ed. Richmond 1990, volume 37 ed. Rubingh 1991 and volume 53 eds. Cross and Singer 1994, Marcel Dekker Inc. New York".

The fabric softening compounds are preferably compounds that provide excellent softening, and are characterised by a chain melting L$\beta$ to L$\alpha$ transition temperature greater than 25° C., preferably greater than 35° C., most preferably greater than 45° C. This L$\beta$ to L$\alpha$ transition can be measured by differential scanning calorimetry as defined in "Handbook of Lipid Bilayers", D Marsh, CRC Press, Boca Raton, Fla., 1990 (pages 137 and 337).

Substantially water-insoluble fabric softening compounds are defined as fabric softening compounds having a solubility of less than $1 \times 10^{-3}$ wt % in demineralised water at 20° C. Preferably the fabric softening compounds have a solubility of less than $1 \times 10^{-4}$ wt %, more preferably from less than $1 \times 10^{-3}$ to $1 \times 10^{-6}$ wt %.

Especially preferred are cationic fabric softening compounds that are water-insoluble quaternary ammonium materials having two C12-22 alkyl or alkenyl groups connected to the molecule via at least one ester link, preferably two ester links. Di(tallowoxyloxyethyl) dimethyl ammonium chloride and/or its hardened tallow analogue is an especially preferred compound of this class.

A second preferred type comprises those derived from triethanolamine (hereinafter referred to as 'TEA quats') as described in for example U.S. Pat. No. 3,915,867. Suitable materials are, for example, N-methyl-N,N,N-triethanolamine ditallowester or di-hardened-tallowester quaternary ammonium chloride or methosulphate. Examples of commercially available TEA quats include Rewoquat WE18 and Rewoquat WE20, both partially unsaturated (ex. WITCO), Tetranyl AOT-1, fully saturated (ex. KAO) and Stepantex VP 85, fully saturated (ex. Stepan).

It is advantageous if the quaternary ammonium material is biologically biodegradable.

It is also possible to include certain mono-alkyl cationic surfactants which can be used in main-wash compositions for fabrics. Cationic surfactants that may be used include quaternary ammonium salts of the general formula R1R2R3R4N+X— wherein the R groups are long or short hydrocarbon chains, typically alkyl, hydroxyalkyl or ethoxylated alkyl groups, and X is a counter-ion (for example, compounds in which R1 is a C8-C22 alkyl group, preferably a C8-C10 or C12-C14 alkyl group, R2 is a methyl group, and R3 and R4, which may be the same or different, are methyl or hydroxyethyl groups); and cationic esters (for example, choline esters).

The choice of surface-active compound (surfactant), and the amount present, will depend on the intended use of the detergent composition. In fabric washing compositions, different surfactant systems may be chosen, as is well known to the skilled formulator, for hand-washing products and for products intended for use in different types of washing machine.

The total amount of surfactant present will also depend on the intended end use and may, in fully formulated products, be as high as 60 wt %, for example, in a composition for washing fabrics by hand. In compositions for machine washing of fabrics, an amount of from 5 to 40 wt % is generally appropriate. Typically compositions will comprise at least 2 wt % surfactant e.g. 2 to 60 wt %, preferably 15 to 40 wt % most preferably 25 to 35 wt %.

Detergent compositions suitable for use in most automatic fabric washing machines generally contain anionic non-soap surfactant, or non-ionic surfactant, or combinations of the two in any suitable ratio, optionally together with soap.

Compositions, when used as main wash fabric washing compositions, will generally also contain one or more detergency builders. The total amount of detergency builder in compositions will typically range from 5 to 80 wt %, preferably from 10 to 60 wt % of composition.

Inorganic builders that may be present include sodium carbonate, if desired in combination with a crystallisation seed for calcium carbonate, as disclosed in GB 1 437 950 (Unilever); crystalline and amorphous aluminosilicates, for example, zeolites as disclosed in GB 1 473 201 (Henkel), amorphous aluminosilicates as disclosed in GB 1 473 202 (Henkel) and mixed crystalline/amorphous aluminosilicates as disclosed in GB 1 470 250 (Procter & Gamble); and layered silicates as disclosed in EP 164 514B (Hoechst). Inorganic phosphate builders, for example, sodium orthophosphate, pyrophosphate and tripolyphosphate are also suitable for use with this invention.

The compositions preferably contain an alkali metal, preferably sodium, aluminosilicate builder. Sodium aluminosilicates may generally be incorporated in end product formulations amounts of from 10 to 70 wt % (anhydrous basis), preferably from 25 to 50 wt %.

The alkali metal aluminosilicate may be either crystalline or amorphous or mixtures thereof, having the general formula: 0.8 1.5 $Na_2O$. $Al_2O_3$. 0.8 6 $SiO_2$.

These materials contain some bound water and are required to have a calcium ion exchange capacity of at least 50 mg CaO/g. The preferred sodium aluminosilicates contain 1.5 3.5 $SiO_2$ units (in the formula above). Both the amorphous and the crystalline materials can be prepared readily by reaction between sodium silicate and sodium aluminate, as amply described in the literature. Suitable crystalline sodium aluminosilicate ion exchange detergency builders are described, for example, in GB 1 429 143 (Procter & Gamble). The preferred sodium aluminosilicates of this type are the well known commercially available zeolites A and X, and mixtures thereof.

The zeolite may be the commercially available zeolite 4A now widely used in laundry detergent powders. However, according to a preferred embodiment of the invention, the zeolite builder incorporated in the compositions for use in the invention is maximum aluminium zeolite P (zeolite MAP) as described and claimed in EP 384 070A (Unilever). Zeolite MAP is defined as an alkali metal aluminosilicate of the zeolite P type having a silicon to aluminium weight ratio not exceeding 1.33, preferably within the range of from 0.90 to 1.33, and more preferably within the range of from 0.90 to 1.20.

Especially preferred is zeolite MAP having a silicon to aluminium weight ratio not exceeding 1.07, more preferably about 1.00. The calcium binding capacity of zeolite MAP is generally at least 150 mg CaO per g of anhydrous material.

Organic builders that may be present include polycarboxylate polymers such as polyacrylates, acrylic/maleic copolymers, and acrylic phosphinates; monomeric polycarboxylates such as citrates, gluconates, oxydisuccinates, glycerol mono, di ¬ and trisuccinates, carboxymethyloxy succinates, carboxymethyloxymalonates, dipicolinates, hydroxyethyliminodiacetates, alkyl and alkenylmalonates and succinates; and sulphonated fatty acid salts. This list is not intended to be exhaustive.

Especially preferred organic builders are citrates, suitably used in fully formulated compositions in amounts of from 5 to 30 wt %, preferably from 10 to 25 wt %; and acrylic polymers, more especially acrylic/maleic copolymers, suitably used in amounts of from 0.5 to 15 wt %, preferably from 1 to 10 wt %.

Builders, both inorganic and organic, are preferably present in alkali metal salt, especially sodium salt, form.

Compositions comprising particles for use in the invention may also suitably contain a bleach system. Fabric washing compositions may desirably contain peroxy bleach compounds, for example, inorganic persalts or organic peroxyacids, capable of yielding hydrogen peroxide in aqueous solution.

Suitable peroxy bleach compounds include organic peroxides such as urea peroxide, and inorganic persalts such as the alkali metal perborates, percarbonates, perphosphates, persilicates and persulphates. Preferred inorganic persalts are sodium perborate monohydrate and tetrahydrate, and sodium percarbonate.

Especially preferred is sodium percarbonate having a protective coating against destabilisation by moisture. Sodium percarbonate having a protective coating comprising sodium metaborate and sodium silicate is disclosed in GB 2 123 044B (Kao).

The peroxy bleach compound is suitably present in a fully formulated product in an amount of from 0.1 to 35 wt %, preferably from 0.5 to 25 wt %. The peroxy bleach compound may be used in conjunction with a bleach activator (bleach precursor) to improve bleaching action at low wash temperatures. The bleach precursor is suitably present in an amount of from 0.1 to 8 wt %, preferably from 0.5 to 5 wt %.

Preferred bleach precursors are peroxycarboxylic acid precursors, more especially peracetic acid precursors and pernoanoic acid precursors. Especially preferred bleach precursors suitable for use in the present invention are N,N,N', N', tetracetyl ethylenediamine (TAED) and sodium nonanoyloxybenzene sulphonate (SNOBS). The novel quaternary ammonium and phosphonium bleach precursors disclosed in U.S. Pat. No. 4,751,015 and U.S. Pat. No. 4,818,426 (Lever Brothers Company) and EP 402 971A (Unilever), and the cationic bleach precursors disclosed in EP 284 292A and EP 303 520A (Kao) are also of interest.

The bleach system can be either supplemented with or replaced by a peroxyacid. Examples of such peracids can be found in U.S. Pat. No. 4,686,063 and U.S. Pat. No. 5,397, 501 (Unilever). A preferred example is the imido peroxycarboxylic class of peracids described in EP A 325 288, EP A 349 940, DE 382 3172 and EP 325 289. A particularly preferred example is phthalimido peroxy caproic acid (PAP). Such peracids are suitably present at 0.1-12% wt, preferably 0.5-10% wt.

A bleach stabiliser (transition metal sequestrant) may also be present in fully formulated products. Suitable bleach stabilisers include ethylenediamine tetra-acetate (EDTA), the polyphosphonates such as Dequest (Trade Mark) and non phosphate stabilisers such as EDDS (ethylene diamine disuccinic acid). These bleach stabilisers are also useful for stain removal especially in end-products containing low levels of bleaching species or no bleaching species.

An especially preferred bleach system comprises a peroxy bleach compound (preferably sodium percarbonate optionally together with a bleach activator), and a transition metal bleach catalyst as described and claimed in EP 458 397A, EP 458 398A and EP 509 787A (Unilever).

Advantageously in the compositions for use in the invention benefit agents, particularly, perfume components may be employed which are sensitive to bleaches as the encapsulation of, for example, the perfume component within the particles will provide some degree of protection to the perfume component or other benefit agent.

The fully formulated compositions may also contain one or more enzyme(s).

Suitable enzymes include the proteases, amylases, cellulases, oxidases, peroxidases and lipases usable for incorporation in detergent compositions. Preferred proteolytic enzymes (proteases) are, catalytically active protein materials which degrade or alter protein types of stains when present as in fabric stains in a hydrolysis reaction. They may be of any suitable origin, such as vegetable, animal, bacterial or yeast origin.

Proteolytic enzymes or proteases of various qualities and origins and having activity in various pH ranges of from 4-12 are available and can be used in the instant invention. Examples of suitable proteolytic enzymes are the subtilisins which are obtained from particular strains of *B. Subtilis B. licheniformis*, such as the commercially available subtilisins Maxatase (Trade Mark), as supplied by Genencor International N.V., Delft, Holland, and Alcalase (Trade Mark), as supplied by Novozymes Industri A/S, Copenhagen, Denmark.

Particularly suitable is a protease obtained from a strain of *Bacillus* having maximum activity throughout the pH range of 8-12, being commercially available, e.g. from Novozymes Industri NS under the registered trade names Esperase (Trade Mark) and Savinase (Trade Mark). The preparation of these and analogous enzymes is described in GB 1 243 785. Other commercial proteases are Kazusase (Trade Mark obtainable from Showa Denko of Japan), Optimase (Trade Mark from Miles Kali Chemie, Hannover, West Germany), and Superase (Trade Mark obtainable from Pfizer of U.S.A.).

Detergency enzymes are commonly employed in fully formulated products in granular form in amounts of from about 0.1 to about 3.0 wt % on product. However, any suitable physical form of enzyme may be used. Advantageously in the compositions for use in the invention benefit agents, for example, perfume components, may be employed which are sensitive to enzymes as the encapsulation of the perfume component (or other benefit agent) within the particles will provide some degree of protection to the perfume component (or other benefit agent).

The compositions for use in the invention may contain alkali metal, preferably sodium carbonate, in order to increase detergency and ease processing. Sodium carbonate may suitably be present in fully formulated products in amounts ranging from 1 to 60 wt %, preferably from 2 to 40 wt %. However, compositions containing little or no sodium carbonate are also within the scope of the invention.

The fully formulated detergent composition when diluted in the wash liquor (during a typical wash cycle) will typically give a pH of the wash liquor from 7 to 10.5 for a main wash detergent.

Particulate detergent compositions are suitably prepared by spray drying a slurry of compatible heat insensitive ingredients, and then spraying on or post-dosing those ingredients unsuitable for processing via the slurry. The skilled detergent formulator will have no difficulty in deciding which ingredients should be included in the slurry and which should not. It is particularly useful to add the perfume particles for use in the present invention via post-dosing.

Particulate detergent compositions preferably have a bulk density of at least 400 g/liter, more preferably at least 500 g/liter. Especially preferred compositions have bulk densities of at least 650 g/liter, more preferably at least 700 g/liter.

Such powders may be prepared either by post tower densification of spray dried powder, or by wholly non tower methods such as dry mixing and granulation; in both cases a high-speed mixer/granulator may advantageously be used. Processes using high speed mixer/granulators are disclosed, for example, in EP 340 013A, EP 367 339A, EP 390 251A and EP 420 317A (Unilever).

Liquid detergent compositions can be prepared by admixing the essential and optional ingredients thereof in any desired order to provide compositions containing components in the requisite concentrations. Liquid compositions for use in the present invention can also be in compact form which means it will contain a lower level of water compared to a conventional liquid detergent.

In order that the present invention may be still further understood and carried forth into practice it will be further described with reference to the following examples:

EXAMPLES

In the following examples, all weights are by weight of the total composition unless otherwise indicated.

Example 1: —Preparation of Particles P1 and P2, in Accordance with the Invention Particles with poly(urethane) shells and acrylate core monomers were designated P1 and P2. P1 had an aromatic poly(benzyl methacrylate) core; P2 had an aliphatic poly(butylmethacrylate) core.

P1 and P2 were prepared by the following method.

1. Poly(phenyl isocyanate), isophorone diisocyanate, butyl methacrylate or benzyl methacrylate, white mineral oil (Sonneborn Blandol) and N,N'-dimethylethanolamine were combined in a vial.
2. SLES-1EO (Texapon N701), Brij 58, 1,1,1-tris(hydroxymethyl)propane, and 1,6-hexane diol were dissolved in water and cooled to below 10° C. in an ice bath.
3. The two phases were mixed and shaken vigorously by hand, then emulsified using a sonic probe for 2×90 seconds at 60% power whilst cooled in an ice bath.
4. The emulsion was placed in a round bottom flask and stirred at an external temperature of 55° C. and 300 rpm.
5. 25 minutes after adding to the flask, Pluronic P65 solution was added over 5 minutes and the mixture stirred for 2 hours.
6. The temperature was increased to 80° C.
7. Ascorbic acid solution (0.43 g ascorbic acid in 2.2 ml water) was added
8. 0.25 g tertiary-butyl-hydroperoxide was dissolved in 5 ml water and the mixture was added via peristaltic pump to the reaction mixture over 45-60 minutes.
9. The mixture was heated for a further 2 hours before cooling.

The compositions of particles P1 and P2, as aqueous dispersions, are given in Table 1.

TABLE 1

Compositions of particles P1 and P2 having poly(benzylmethacrylate) and poly(butylmethacrylate) cores respectively, and a poly(urethane) shell, as aqueous dispersions.

| | amount (g) | |
|---|---|---|
| Ingredient | P1 | P2 |
| Polyurethane components | 16.22 | 13.68 |
| poly(phenyl isocyanate) | 2.98 | 2.98 |
| Isophorone diisocyanate | 6.22 | 6.22 |
| 1,6-Hexane Diol | 3.30 | 3.30 |
| 1,1,1-Tris(hydroxymethyl)propane | 1.18 | 1.18 |
| Benzyl Methacrylate | 0.00 | 10.81 |
| Butyl Methacrylate | 10.81 | 0.00 |
| N,N-Dimethylethanolamine | 0.07 | 0.07 |
| white mineral oil | 3.05 | 3.05 |
| Tertiary-butyl-hydroperoxide (initiator) | 0.25 | 0.25 |
| Ascorbic acid | 0.43 | 0.43 |
| SLES 1EO surfactant | 1.20 | 1.20 |
| Brij 58 surfactant | 2.30 | 2.30 |
| Pluronic P65 | 0.30 | 0.30 |
| Water | 72.1 | 72.1 |

Example 2: —Absorption of Malodour Compounds by Particles P1 and P2

The absorption of malodour compounds (commonly found in underarm sweat) by Particles P1 and P2 was measured by the following methodology: —5 ml volume mixtures containing a 1:1:1 ratio by weight of three volatile fatty acids (VFAs) and electrolytes found in underarm sweat were prepared in the presence of particles P1 and P2, and sealed in Solid Phase Microextraction (SPME) headspace gas chromatography vials.

The total VFA concentrations were 0.1 g/liter, 0.2 g/liter and 0.5 g/liter. The amount of Particles (P1 or P2) used was 20 g/liter solids. Control samples, containing no particles, were prepared in the same manner but substituting water for the particle suspensions. The compositions of the model sweat, and test solutions comprising P1, P2 or water (control) are given in Table 2 below.

TABLE 2

Compositions of model sweat (electrolyte) and volatile fatty acid containing solutions.

| Component (%) | Control samples | P1 and P2 containing samples |
|---|---|---|
| Potassium chloride | 0.056 | 0.056 |
| Sodium bicarbonate | 0.118 | 0.118 |
| Ammonium chloride | 0.021 | 0.021 |
| L(+)-lactic acid | To pH 4 | To pH 4 |
| Volatile fatty acids (1:1:1 mixture) | 0.01 or 0.05 | 0.01 or 0.05 |
| Isovaleric acid | 0.0033 or 0.0167 | 0.0033 or 0.0167 |
| 3-methyl-2-hexenoic acid | 0.0033 or 0.0167 | 0.0033 or 0.0167 |
| 4-methyloctanoic acid | 0.0033 or 0.0167 | 0.0033 or 0.0167 |
| Latex particle solids (P1) or (P2) | 0 | 2.0 |
| High purity distilled water | To 100% | To 100% |

The samples were allowed to equilibrate at ambient temperature for 14 days before analysis. The samples were then randomized and headspace air above the samples was sampled using SPME GC-MS.

Table 3 lists the ratios of the peak areas measured above the Particles containing samples relative to the appropriate control.

TABLE 3

Ratio of SPME GC headspace peak areas over P1 and P2 containing samples to peak areas over the control.

| Volatile fatty acid | Control | P1 | Peak ratio P1 sample relative to control | P2 | Peak ratio P2 relative to control |
|---|---|---|---|---|---|
| 33 ppm Isovaleric acid | 6.1 | 6.2 | 0.67* | 6.3 | 0.75 |
| 33 ppm 3-methyl-2-hexenoic acid | 6.7 | 6.8 | 0.36* | 6.9 | 0.37* |
| 33 ppm 4-methyloctanoic acid | 6.13 | 6.14 | 0.06* | 6.15 | 0.06* |
| 167 ppm Isovaleric acid | 6.19 | 6.20 | 0.73* | 6.21 | 0.75 |
| 167 ppm 3-methyl-2-hexenoic acid | 6.25 | 6.26 | 0.82 | 6.27 | 0.91 |
| 167 ppm 4-methyloctanoic acid | 6.31 | 6.32 | 0.2* | 6.33 | 0.24* |

*A statistically significant reduction in malodour GC peak relative to latex free control at the 95% confidence interval.

It is evident that the inclusion of latex particles (P1) and (P2) significantly reduces the quantities of VFA detectable in the headspace above the mixtures.

Example 3: —Retention of Underarm Sweat Volatile Fatty Acid Mixtures, Following a Change in Humidity, by Antiperspirant Compositions Containing Particles P1 and P2

Retention of underarm sweat volatile fatty acid mixtures (isovaleric acid, 3-methyl-2-hexenoic acid and 4-methyloctanoic acid) by antiperspirant compositions containing Particles P1 or P2, following a change in humidity, was measured as described below.

In order to mimic the conditions present in the underarm during sweating, the release of model malodour compounds from a dried down anti-perspirant product containing Particles P1 or P2 was examined by warming the samples to body temperature and then rapidly changing the humidity of the headspace.

The compositions of the antiperspirant roll-on products (before drying down) are given in Table 4.

TABLE 4

Compositions of unfragranced antiperspirant roll-on compositions comprising Particles P1 or P2; and a particle free control.

| Ingredient | Control | Formulation with P1 | Formulation with P2 |
|---|---|---|---|
| Sunflower oil | 2.0 | 2.0 | 2.0 |
| Steareth-2 | 2.6 | 2.6 | 2.6 |
| Steareth-20 | 0.6 | 0.6 | 0.6 |
| Aluminium chlorohydrate | 15 | 15 | 15 |
| P1 | 0 | 2.0 | 0 |
| P2 | 0 | 0 | 2.0 |
| Water | to 100 | to 100 | to 100 |

1 cm×10 cm strips of woven cotton textile were treated with the compositions given in Table 4 (0.15 g), spreading the formulation evenly across the fabric, and then allowing to air dry.

The textile strips were then treated with 0.15 g of a pH 5 model sweat solution containing 0.5 g/liter total volatile fatty acids, applied evenly across the fabric. The composition of the model sweat was the same as given in Table 2 above, only the pH was adjusted to 5. Isovaleric acid, 3-methyl-2-hexenoic acid and 4-methyloctanoic acid were each present at 0.0167 wt %.

The samples were air dried, wrapped in foil and frozen until shortly before analysis, when they were thawed while still wrapped.

The headspace concentrations of the malodour components present above the treated textiles was measured using an Ionicon Analytik Proton Transfer Reaction Mass Spectrometry-Time of Flight (PTR-TOF 8000) instrument in the H3O+ mode at a drift tube voltage of 600V. The temperatures of the drift chamber and inlet line were set to 80° C. and the pressure in the drift chamber was 2.23 mbar. The cycle time was set to 2 seconds.

The samples were maintained at 35° C. and the dynamic headspace of each sample was measured for 30 minutes flowing dry nitrogen over the samples. Using an Ionicon Gas Calibration Unit, the humidity of the nitrogen was changed to 95% Relative Humidity and measurements were continued for a further 120 minutes.

The malodour components were detected as the following protonated mass ions: isovaleric acid-103.076; 3-methyl-2-hexenoic acid-129.092; 4-methyloctanoic acid-159-139 and the concentration was measured (as the ion yield) over a period of 150 minutes.

Plots of ion yield versus time were generated and the areas under the curves were estimated using the Trapezoid Rule (Area=☐[(average Ion Yield in a given time increment)× (time increment duration)]. This integration process was carried out over the time period of 0-30 minutes (when the sample was exposed to dry air) and 30 to 120 minutes (when the sample was exposed to the damp air). Two replicate samples were compared and the results are listed in Table 5.

TABLE 5

Release of volatile fatty acids from Particle-containing and Particle free AP roll-on under dry and humid conditions (integrated peak areas).

| Formulation | Malodour component | Area (dry) | Area (95% RH) |
|---|---|---|---|
| Latex free formulation | Isovaleric acid | $5.55 \times 10^{10}$ $6.77 \times 10^{10}$ | $7.76 \times 10^{11}$ $7.18 \times 10^{11}$ |
| Latex free formulation | 3-methyl-2-hexenoic acid | $4.90 \times 10^{10}$ $6.44 \times 10^{10}$ | $2.24 \times 10^{12}$ $2.10 \times 10^{12}$ |
| Latex free formulation | 4-methyl-octanoic acid | $4.02 \times 10^{10}$ $1.89 \times 10^{10}$ | $5.91 \times 10^{11}$ $5.2 \times 10^{11}$ |
| Formulation with 2% latex (7) | Isovaleric acid | $2.01 \times 10^{10}$ $2.11 \times 10^{10}$ | $4.98 \times 10^{11}$ $6.16 \times 10^{11}$ |
| Formulation with 2% latex (7) | 3-methyl-2-hexenoic acid | $2.00 \times 10^{10}$ $2.26 \times 10^{10}$ | $1.18 \times 10^{12}$ $1.59 \times 10^{12}$ |
| Formulation with 2% latex (7) | 4-methyl-octanoic acid | $1.11 \times 10^{10}$ $1.62 \times 10^{10}$ | $1.79 \times 10^{11}$ $2.69 \times 10^{11}$ |
| Formulation with 2% latex (8) | Isovaleric acid | $1.38 \times 10^{10}$ $9.32 \times 10^{9}$ | $3.41 \times 10^{11}$ $2.70 \times 10^{11}$ |
| Formulation with 2% latex (8) | 3-methyl-2-hexenoic acid | $6.05 \times 10^{9}$ $9.43 \times 10^{9}$ | $7.14 \times 10^{11}$ $6.06 \times 10^{11}$ |
| Formulation with 2% latex (8) | 4-methyl-octanoic acid | $1.47 \times 10^{9}$ $7.00 \times 10^{9}$ | $6.24 \times 10^{10}$ $7.97 \times 10^{10}$ |

Table 6 shows a comparison of the mean integrated peak areas obtained for the formulations under the dry and humid conditions.

TABLE 6

Mean integrated peak areas for the formulations under the dry and humid conditions

| Formulation | Malodour component | Area (dry) | Area (95% RH) |
|---|---|---|---|
| Latex free formulation | Isovaleric acid | $6.16 \times 10^{10}$ | $7.47 \times 10^{11}$ |
| Formulation with 2% latex (7) | Isovaleric acid | $2.06 \times 10^{10}$ * | $5.57 \times 10^{11}$ * |
| Formulation with 2% latex (8) | Isovaleric acid | $1.16 \times 10^{10}$ * | $3.05 \times 10^{11}$ * |
| Latex free formulation | 3-methyl-2-hexenoic acid | $5.67 \times 10^{10}$ | $2.17 \times 10^{12}$ |
| Formulation with 2% latex (7) | 3-methyl-2-hexenoic acid | $2.13 \times 10^{10}$ * | $1.39 \times 10^{12}$ * |
| Formulation with 2% latex (8) | 3-methyl-2-hexenoic acid | $7.74 \times 10^{9}$ * | $6.60 \times 10^{11}$ |
| Latex free formulation | 4-methyl-octanoic acid | $2.96 \times 10^{10}$ | $5.56 \times 10^{11}$ |
| Formulation with 2% latex (7) | 4-methyl-octanoic acid | $1.36 \times 10^{10}$ * | $2.24 \times 10^{11}$ * |
| Formulation with 2% latex (8) | 4-methyl-octanoic acid | $4.24 \times 10^{9}$ * | $7.10 \times 10^{10}$ * |

* A statistically significant reduction in malodour GC peak relative to latex free control at the 95% confidence interval.

A comparison of the data generated under dry conditions and at 95% RH shows that there is an increase in the integrated peak areas as the humidity is raised. However, incorporation of Particles P1 and P2 cause a significant decrease in the integrated peak areas relative to the latex free controls under both the dry and humid conditions. The effect is particularly marked for Particle P2.

Thus, the particles for use in the invention are effective in retaining the malodour compounds in the presence of a formulation and they can provide malodour control even when further sweating occurs.

Example 4: —Retention of Volatile Fatty Acid Mixtures, Following a Change in Humidity, by Leave-in Hair Conditioner Compositions Containing Particle P1

In order to mimic the conditions present on the scalp during sweating, the release of model malodour compounds from a dried down leave-on hair conditioner composition containing Particle P1 was examined by warming the samples to body temperature and then changing the humidity of the headspace, as in Example 3.

Unfragranced leave-on hair conditioner base containing 2% w/w P1 solids was prepared together with a particle-free control formulation and applied to 1 cm×10 cm strips of woven cotton textile as described in Example 3.

The compositions of the leave-on hair conditioners are given in Table 7.

TABLE 7

Compositions of leave-on hair conditioner with and without Particle P1

| Ingredient | % inclusion | |
|---|---|---|
| Lactic acid | 0.32 | 0.32 |
| Stearyl alcohol | 5.00 | 5.00 |
| Behenyl trimethyl ammonium chloride (BTAC) | 0.875 | 0.875 |
| Stearamidopropyl dimethylamine | 1.25 | 1.25 |
| Potassium chloride | 0.1 | 0.1 |
| Ethylenediamine tetra-acetic acid, disodium salt | 0.1 | 0.1 |
| Methylchloroisothiazolinone, methylisothiazolinone (Kathon CG) | 0.04 | 0.04 |
| DMDA Hydantoin (Glydant) | 0.055 | 0.055 |
| P1 | 0 | 2.00 |
| Water | to 100 | to 100 |

The textile strips were then treated with a model sweat solution containing model volatile fatty acid malodours, air dried and packaged as described in Example 3.

The headspace concentrations of the malodour components present above the treated textiles were measured using PTR-MS using the protocol described in Example 3.

Plots of ion yield versus time were generated and the areas under the curves were integrated over the periods 0-30 minutes (dry air) and 30 to 120 minutes (damp air) as described for Example 3. Two replicate samples were compared and the results are listed in Table 8.

TABLE 8

Release of volatile fatty acids from hair conditioner with and without P1 under dry and humid conditions (integrated peak areas)

| Formulation | Malodour component | Area (dry) | Area (95% RH) |
|---|---|---|---|
| Particle free formulation | Isovaleric acid | $2.78 \times 10^9$ $1.47 \times 10^9$ | $3.69 \times 10^{10}$ $3.32 \times 10^{10}$ |
| Particle free formulation | 3-methyl-2-hexenoic acid | $3.36 \times 10^8$ $2.77 \times 10^8$ | $2.52 \times 10^{10}$ $3.08 \times 10^{10}$ |
| Particle free formulation | 4-methyl-octanoic acid | $1.26 \times 10^7$ $1.33 \times 10^7$ | $1.23 \times 10^9$ $1.57 \times 10^9$ |
| Formulation with 2% P1 | Isovaleric acid | $2.76 \times 10^9$ $1.48 \times 10^9$ | $2.03 \times 10^{10}$ $2.42 \times 10^{10}$ |
| Formulation with 2% P1 | 3-methyl-2-hexenoic acid | $4.69 \times 10^8$ $2.02 \times 10^8$ | $1.43 \times 10^{10}$ $1.54 \times 10^{10}$ |
| Formulation with 2% P1 | 4-methyl-octanoic acid | $3.79 \times 10^7$ $4.52 \times 10^7$ | $5.09 \times 10^8$ $7.14 \times 10^8$ |

Table 9 shows a comparison of the mean integrated peak areas obtained for the particle free control and P1 containing formulations under the dry and humid conditions.

TABLE 9

Mean integrated peak areas for the particle free control and P1 containing formulations under the dry and humid conditions.

| Formulation | Malodour component | Area (dry) | Area (95% RH) |
|---|---|---|---|
| Particle free formulation | Isovaleric acid | $2.13 \times 10^9$ | $3.51 \times 10^{10}$ |
| 2% P1 | Isovaleric acid | $2.12 \times 10^9$ | $2.23 \times 10^{10}$ * |
| Particle free formulation | 3-methyl-2-hexenoic acid | $3.06 \times 10^8$ | $2.80 \times 10^{10}$ |
| 2% P1 | 3-methyl-2-hexenoic acid | $3.36 \times 10^8$ | $1.48 \times 10^{10}$ * |
| Particle free formulation | 4-methyl-octanoic acid | $1.30 \times 10^7$ | $1.40 \times 10^9$ |
| 2% P1 | 4-methyl-octanoic acid | $4.16 \times 10^7$ | $5.11 \times 10^8$ * |

* A statistically significant reduction in malodour GC peak relative to latex free control at the 95% confidence interval.

A comparison of the data generated under dry conditions and at 95% RH show that there is an increase in the integrated peak areas as the humidity is raised. However, incorporation of Particles P1 causes a significant decrease in the integrated peak areas relative to the latex free controls under both the dry and humid conditions.

This demonstrates that the Particles P1 are effective in retaining the malodour compounds in the presence of a leave-on hair conditioner formulation and they can provide malodour control even when further sweating or malodour generation occurs.

The invention claimed is:

1. A method of absorbing malodour compound from a substrate, the method comprising:
applying to a substrate a composition in which are present particles comprising:
(a) a solid core comprising a first hydrophobic polymer, and
(b) a shell comprising a second hydrophobic polymer wherein the Tg of the first hydrophobic polymer is lower than the Tg of the second hydrophobic polymer; wherein the particles have a mean particle size of less than 1 micron,
wherein malodour compound is absorbed from the substrate and retained by the particles.

2. The method as claimed in claim 1, wherein the core comprises a polyacrylate polymer.

3. The method as claimed in claim 2, wherein the polyacrylate polymer is selected from the group consisting of polybutyl methacrylate, polybenzyl methacrylate, poly lauryl methacrylate, poly-2-hydroxyethyl methacrylate, poly-2-hydroxypropyl methacrylates and mixtures thereof.

4. The method as claimed in claim 1 wherein the shell comprises a polymer selected from a polyurea and a polyurethane.

5. The method as claimed in claim 4, wherein the shell comprises polyurethane formed from reaction of diisocyanate with diol and cross-linked with polyamine or polyol.

6. The method as claimed in claim 1 wherein the core further comprises a benefit agent.

7. The method as claimed in claim 1 wherein the benefit agent is selected from a fragrance, a skin care agent, an anti-oxidant, a vitamin, an anti-bacterial agent, an anti-inflammatory active, an anti-perspirant, a skin conditioning agent, a sunscreen and mixtures thereof.

8. The method as claimed in claim 7, wherein the benefit agent is a fragrance.

9. The method as claimed in claim 1 wherein the particle comprises a second shell.

10. The method as claimed in claim 1 wherein the particle comprises a deposition aid.

11. The method as claimed in claim 1 wherein the composition further comprises an active ingredient.

12. The method claimed in claim 11, wherein the composition is a home or personal care composition, selected from a deodorant, antiperspirant, shampoo, hair conditioner, skin care, skin cleansing product, a laundry detergent, laundry conditioner, a hard surface cleaner, floor cleaners and a soft surface refresher.

13. The method as claimed in claim 11 wherein the active ingredient is selected from a surfactant, a cleaning agent, a solvent, a polymer, an antiperspirant active and mixtures thereof.

14. The method as claimed in claim 12, wherein the composition is suitable for the treatment of skin and/or hair.

15. The method as claimed in claim 1 wherein the malodour compound comprises volatile fatty acids.

16. The method as claimed in claim 1 wherein the particles have a mean particle size of from 0.1 to 0.3 microns.

17. The method as claimed in claim 1 wherein the malodour compound comprises isovaleric acid, 3-methyl-2-hexanoic acid and 4-methyloctanoic acid.

* * * * *